United States Patent
Fevig et al.

(10) Patent No.: US 8,093,257 B2
(45) Date of Patent: Jan. 10, 2012

(54) [6,5]-BICYCLIC GPR119 G PROTEIN-COUPLED RECEPTOR AGONISTS

(75) Inventors: John M. Fevig, Doylestown, PA (US); Dean A. Wacker, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 660 days.

(21) Appl. No.: 12/112,053

(22) Filed: Apr. 30, 2008

(65) Prior Publication Data

US 2009/0018055 A1    Jan. 15, 2009

Related U.S. Application Data

(60) Provisional application No. 60/915,952, filed on May 4, 2007.

(51) Int. Cl.
*A01N 43/90* (2006.01)
*A61K 31/519* (2006.01)
*C07D 471/00* (2006.01)
*C07D 487/00* (2006.01)
*C07D 491/00* (2006.01)

(52) U.S. Cl. .................................. 514/261.1; 544/254

(58) Field of Classification Search .................. None
See application file for complete search history.

(56) References Cited

U.S. PATENT DOCUMENTS

| | | | |
|---|---|---|---|
| 3,826,643 A | 7/1974 | Diehl et al. | |
| 5,488,064 A | 1/1996 | Sher | |
| 5,491,134 A | 2/1996 | Sher et al. | |
| 5,541,204 A | 7/1996 | Sher et al. | |
| 5,612,359 A | 3/1997 | Murugesan | |
| 5,770,615 A | 6/1998 | Cheng et al. | |
| 5,776,983 A | 7/1998 | Washburn et al. | |
| 6,043,265 A | 3/2000 | Murugesan et al. | |
| 6,566,384 B1 | 5/2003 | Owen et al. | |
| 2003/0181420 A1 | 9/2003 | Bayne et al. | |
| 2005/0080111 A1 | 4/2005 | Bayne et al. | |
| 2005/0245515 A1 | 11/2005 | Dehmlow et al. | |
| 2006/0155128 A1 | 7/2006 | Jones et al. | |
| 2006/0292073 A1 | 12/2006 | Goodman et al. | |

FOREIGN PATENT DOCUMENTS

| | | |
|---|---|---|
| EP | 1 338 651 | 8/2003 |
| WO | WO 96/38144 | 12/1996 |
| WO | WO 97/12613 | 4/1997 |
| WO | WO 97/12615 | 4/1997 |
| WO | WO 99/26659 | 6/1999 |
| WO | WO 00/01389 | 1/2000 |
| WO | WO 00/39102 | 7/2000 |
| WO | WO 02/02519 | 1/2002 |
| WO | WO 2004/065380 | 8/2004 |
| WO | WO 2004/076413 | 9/2004 |
| WO | WO 2004/089885 | 10/2004 |
| WO | WO 2005/007647 | 1/2005 |
| WO | WO 2005/007658 | 1/2005 |
| WO | WO 2005/025504 | 3/2005 |
| WO | WO 2005/089786 | 9/2005 |
| WO | WO 2005/121121 | 12/2005 |
| WO | WO 2006/067532 | 6/2006 |
| WO | WO 2006/083491 | 8/2006 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Donetti, A. et al., "(Imidazolylphenyl)formamidines. A Structurally Novel Class of Potent Histamine $H_2$ Antagonists", J. Med. Chem., vol. 27, No. 3, pp. 380-386 (1984).
Gomtsyan, A. et al., "Design, Synthesis, and Structure-Activity Relationship of 6-Alkynylpyrimidines as Potent Adenosine Kinase Inhibitors", J. Med. Chem., vol. 45, No. 17, pp. 3639-3648 (2002).
Ahrén, B., "Autonomic regulation of islet hormone secretion—Implications for health and disease", Diabetologia, vol. 43, pp. 393-410 (2000).
Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001). Boger, D.L. et al., "Total Syntheses of Azafluoranthene Alkaloids: Rufescine and Imeluteine", J. Org. Chem., vol. 49, No. 21, pp. 4050-4055 (1984).
Brancati, F.L. et al., "Body Weight Patterns from 20 to 49 Years of Age and Subsequent Risk for Diabetes Mellitus", Arch. Intern. Med., vol. 159, pp. 957-963 (1999).
Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).
Bundgaard, H., ed., Design of Prodrugs, Elsevier Science Publishers B.V., publ. (1985) (table of contents).
Butler, A.E. et al., "β-Cell Deficit and Increased β-Cell Apoptosis in Humans with Type 2 Diabetes", Diabetes, vol. 52, pp. 102-110 (2003).

(Continued)

*Primary Examiner* — Jeffrey Murray
(74) *Attorney, Agent, or Firm* — Terence J. Bogie

(57) ABSTRACT

Novel compounds are provided which are GPR119 G protein-coupled receptor modulators. GPR119 G protein-coupled receptor modulators are useful in treating, preventing, or slowing the progression of diseases requiring GPR119 G protein-coupled receptor modulator therapy. These novel compounds have the structure:

(I)

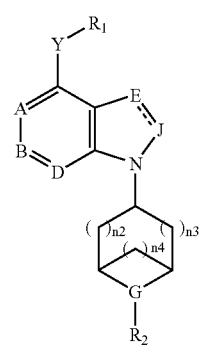

or stereoisomers or prodrugs or pharmaceutically acceptable salts thereof, wherein $n_2$, $n_3$, $n_4$, A, B, D, E, G, J, Y, $R_1$ and $R_2$ are defined herein.

10 Claims, No Drawings

OTHER PUBLICATIONS

Chu, Z.-L. et al., "A Role for β-Cell-Expressed G Protein-Coupled Receptor 119 in Glycemic Control by Enhancing Glucose-Dependent Insulin Release", Endocrinology, vol. 148, No. 6, pp. 2601-2609 (2007).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Deng, H. et al., "Aryllead(IV) Reagents in Synthesis: Formation of the C11 Quaternary Center of N-Methylwelwitindolinone C Isothiocyanate", Organic Letters, vol. 3, No. 19, pp. 3001-3004 (2001).

Ford, E.S. et al., "Prevalence of the Metabolic Syndrome Among US Adults", Journal of the American Medical Association, vol. 287, No. 3, pp. 356-359 (2002).

Fredriksson, R. et al., "Seven evolutionary conserved human rhodopsin G protein-coupled receptors lacking close relatives", FEBS Letters, vol. 554, pp. 381-388 (2003).

Frlan, R. et al., "Recent Progress in Diaryl Ether Synthesis", Synthesis, No. 14, pp. 2271-2285 (2006).

Gennaro, A.R., ed., Remington's Pharmaceutical Sciences, 17th Edition, Mack Publishing Company, publ., p. 1418 (1985).

Greene, T.W. et al., Protective Groups in Organic Synthesis, Second Edition, John Wiley & Sons, Inc., publ., pp. ix-x (table of contents) (1991).

Haning, H. et al., "Novel heterocyclic thyromimetics", Bioorganic & Medicinal Chemistry Letters, vol. 15, pp. 1835-1840 (2005).

Hara, S., "Ileal Na+/bile acid cotransporter inhibitors", Drugs of the Future, vol. 24, No. 4, pp. 425-430 (1999).

Hertzog, D.L., "Recent advances in the cannabinoids", Expert Opin. Ther. Patents, vol. 14, No. 10, pp. 1435-1452 (2004).

Hill, J.O. et al., "Environmental Contributions to the Obesity Epidemic", Science, vol. 280, pp. 1371-1374 (1998).

Hong, C.Y. et al., "Asymmetric Synthesis of Either Enantiomer of Opium Alkaloids and Morphinans. Total Synthesis of (−)- and (+)-Dihydrocodeinone and (−)- and (+)-Morphine", J. Am. Chem. Soc., vol. 115, No. 23, pp. 11028-11029 (1993).

Itoh, T. et al., "A General Palladium-Catalyzed Coupling of Aryl Bromides/Triflates and Thiols", Organic Letters, vol. 6, No. 24, pp. 4587-4590 (2004).

Jiang, G. et al., "Prevention of obesity in mice by antisense oligonucleotide inhibitors of stearoyl-CoA desaturase-1", The Journal of Clinical Investigation, vol. 115, No. 4, pp. 1030-1038 (2005).

Justus, K. et al., "First Synthesis of a Strained 14-Membered Biaryl Ether Lactone by Macrolactonization", Tetrahedron Letters, vol. 32, No. 14, pp. 5781-5784 (1991).

Katritzky, A.R. et al., "Efficient Transformations of Aldehydes and Ketones into One-Carbon Homologated Carboxylic Acids", Synthesis, pp. 1425-1427 (1996).

Ketcha, D.M. et al., "The Reduction of N-(phenylsulfonyl)indoles with Sodium Cyanoborohydride in Trifluoroacetic Acid", Tetrahedron Letters, vol. 30, No. 49, pp. 6833-6836 (1989).

Le Stunff, C. et al., "Early Changes in Postprandial Insulin Secretion, Not in Insulin Sensitivity, Characterize Juvenile Obesity", Diabetes, vol. 43, pp. 696-702 (1994).

Magnus, P. et al., "Studies on the Synthesis of the Antitumor Agent CC-1065. Synthesis of the Unprotected Cyclopropapyrroloindole a Portion Using the 3,3'-Bipyrrole Strategy", J. Am. Chem. Soc., vol. 109, No. 9, pp. 2706-2711 (1987).

NCBI Entrez Accession No. AAP72125 (gi:32165516), Fredriksson, R. et al., Dec. 8, 2003.

NCBI Entrez Accession No. AY288423 (gi:32165529), Fredriksson, R. et al., Dec. 8, 2003.

Nishio, T. et al., "Reduction of Indolin-2-ones and Desulfurization of Indoline-2-thiones to Indoline and Indole Derivatives", Helvetica Chimica Acta, vol. 73, pp. 1719-1723 (1990).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., vol. 43, No. 22, pp. 4288-4312 (2000).

Overton, H.A. et al., "Deorphanization of a G protein-coupled receptor for oleoylethanolamide and its use in the discovery of small-molecule hypophagic agents", Cell Metabolism, vol. 3, pp. 167-175 (2006).

Pedersen, O., "The Impact of Obesity on the Pathogenesis of Non-Insulin-Dependent Diabetes Mellitus: A Review of Current Hypotheses", Diabetes/Metabolism Reviews, vol. 5, No. 6, pp. 495-509 (1989).

Perry, I.J. et al., "Prospective study of risk factors for development of non-insulin dependent diabetes in middle aged British men", BMJ, vol. 310, pp. 560-564 (1995).

Prentki, M. et al., "Islet β cell failure in type 2 diabetes", The Journal of Clinical Investigation, vol. 116, No. 7, pp. 1802-1812 (2006).

Radinov, R. et al., "Lithiation of Polychloropyrimidines and Dichloropyridines", J. Org. Chem., vol. 56, No. 15, pp. 4793-4796 (1991).

Schubert, U., "The Homologation of Hagemann's Ester", Synthesis, pp. 364-365 (1978).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sirowej, H. et al., "Preparation of substituted indoles by reduction of isatin and oxindole derivatives with diborane/tetrahydrofuran", Synthesis, No. 2, p. 84 (1972).

Soga, T. et al., "Lysophosphatidylcholine enhances glucose-dependent insulin secretion via an orphan G-protein-coupled receptor", Biochemical and Biophysical Research Communications, vol. 326, pp. 744-751 (2005).

Takahashi, K. et al., "Efficient Method for a One-Carbon Homologation of Aldehydes and Benzophenone to Carboxylic Acids", J. Org. Chem., vol. 48, No. 20, pp. 3566-3569 (1983).

Testa, B. et al., Hydrolysis in Drug and Prodrug Metabolism: Chemistry, Biochemistry, and Enzymology, Wiley-VCH GmbH & Co., publ., pp. xi-xx (table of contents) (2003).

Urgaonkar, S. et al., "Application of a New Bicyclic Triaminophosphine Ligand in Pd-Catalyzed Buchwald-Hartwig Amination Reactions of Aryl Chlorides, Bromides, and Iodides", J. Org. Chem. vol. 68, No. 22, pp. 8416-8423 (2003).

Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).

Yang, B.H. et al., "Palladium-catalyzed amination of aryl halides and sulfonates", Journal of Organometallic Chemistry, vol. 576, pp. 125-146 (1999).

Young, S.D. et al., "L-743,726 (DMP-266): a Novel, Highly Potent Nonnucleoside Inhibitor of the Human Immunodeficiency Virus Type 1 Reverse Transcriptase", Antimicrobial Agents and Chemotherapy, vol. 39, No. 12, pp. 2602-2605 (1995).

Zhang, X. et al., "Dimethyldioxirane Oxidation of Indole Derivatives. Formation of Novel Indole-2,3-epoxides and a Versatile Synthetic Route to Indolinones and Indolines", J. Am. Chem. Soc., vol. 115, No. 19, pp. 8867-8868 (1993).

* cited by examiner

[6,5]-BICYCLIC GPR119 G PROTEIN-COUPLED RECEPTOR AGONISTS

RELATED APPLICATION

This application claims the benefit of U.S. Provisional Application No. 60/915,952, filed on May 4, 2007, incorporated herein by reference in its entirety.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., *Diabetes*, 43:696-702 (1989)). However, over time, β-cell function deteriorates and non-insulin-dependent diabetes develops in about 20% of the obese population (Pederson, P., *Diab. Metab. Rev.*, 5:505-509 (1989)) and (Brancati, F. L. et al., *Arch. Intern. Med.*, 159:957-963 (1999)). Given its high prevalence in modern societies, obesity has thus become the leading risk factor for NIDDM (Hill, J. O. et al., *Science*, 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., *BMJ*, 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", *J. Clin. Invest.*, 116:1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cell apoptosis in humans with type 2 diabetes", *Diabetes*, 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Ahren, B., "Autonomic regulation of islet hormone secretion—Implications for health and disease", *Diabetologia*, 43:393-410 (2003)). Those GPCRs specifically coupled to the elevation of cAMP via the G, alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in $K^+$ efflux depolarizes the β-cell leading to an influx of $Ca^{++}$ which promotes the release of insulin.

GPR119 (e.g., human GPR119, GenBank® Accession No. AAP72125 and alleles thereof; e.g., mouse GPR119, GenBank® Accession No. AY288423 and alleles thereof) is a GPCR located at chromosome position Xp26.1 (Fredricksson, R. et al., "Seven evolutionarily conserved human rhodopsin C protein-coupled receptors lacking close relatives", *FEBS Lett.*, 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.*, 326:744-751 (2005), International Applications WO 04/065380, WO 04/076413, WO 05/007647, WO 05/007658, WO 05/121121, WO 06/083491, and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan G-protein-coupled receptor", *Biochem. Biophys. Res. Comm.*, 326:744-751 (2005); Chu, Z. L. et al., "A role for β-cell-expressed GPR119 in glycemic control by enhancing glucose-dependent insulin release", *Endocrinology* (2007) doi:10.1210/en.2006-1608).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for β-cell-expressed GPR119 in glycemic control by enhancing glucose-dependent insulin release", *Endocrinology* (2007) doi:10.1210/en.2006-1608). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism*, 3:167-175 (2006), WO 05/007647, WO 05/007658).

SUMMARY OF THE INVENTION

In accordance with the present invention, aryl and heterocyclyl and related compounds are provided that have the general structure of formula I:

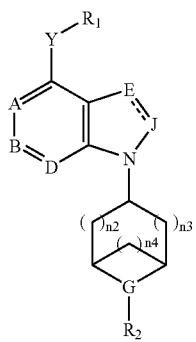

Formula I wherein $n_2$, $n_3$, $n_4$, A, B, D, E, G, J, Y, $R_1$ and $R_2$ are defined below.

Compounds of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma. In general, tested compounds of the instant invention show GPR119 functional activity with an $EC_{50}$ of <10 µM.

The present invention provides compounds of Formula I, pharmaceutical compositions employing such compounds, and methods of using such compounds. In particular, the present invention provides a pharmaceutical composition comprising a therapeutically effective amount of a compound of Formula I, alone or in combination with a pharmaceutically acceptable carrier.

Further, in accordance with the present invention, a method is provided for preventing, modulating, or treating the progression or onset of diseases or disorders associated with the activity of the GPR119 G protein-coupled receptor, such as defined above and hereinafter, wherein a therapeutically effective amount of a compound of Formula I is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I and another compound of Formula I and/or at least one other type of therapeutic agent, is administered to a mammalian, i.e., human, patient in need of treatment.

DESCRIPTION OF THE INVENTION

In accordance with the present invention, compounds of formula I are provided

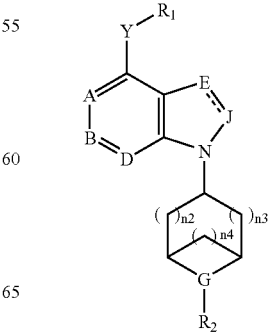

(I)

and enantiomers, diastereomers and pharmaceutically acceptable salts thereof wherein:

A, B and D are independently $CR_{4b}$ or N, provided that at least one A, B or D is N;

E is selected from the group consisting of $CR^9R^9$, $CR^9$, O, N and NH (with a more particular group being $CH_2$, CH, O, N and NH);

G is CH or N;

J is $CR_9R_9$, $CR_9$, C=O, C=S or N;

the dashed line represents an optional double bond, provided that J is not C=O, C=S or $CR_9R_9$ when a double bond is present;

Y is —$NR_3$, O or S;

$n_2$ and $n_3$ are each independently selected from 0-2;

$n_4$ is 0-3;

$R_1$ is aryl or heteroaryl, each of which may optionally be substituted with one or more substituents selected from $R_4$ (more particularly 1-5 of $R_4$);

$R_2$ is selected from the group consisting of cycloalkyl, aryl, heteroaryl, heterocyclyl, C(=O)$R_5$ and —C(=O)O$R_5$, wherein the cycloalkyl, aryl, heteroaryl and heterocyclyl may each be optionally substituted with one or more $R_6$'s (particularly 1-5) $R_6$'s;

$R_3$ is selected from the group consisting of hydrogen, alkyl, alkoxy, cycloalkyl, aryl, arylalkyl, heteroaryl, heteroarylalkyl, heterocyclyl and heterocyclylalkyl (particularly wherein the heteroaryl, heteroarylalkyl, heterocyclyl and heterocyclylalkyl each contain 1-4 heteroatoms selected from N, O and S);

$R_4$, at each occurrence, is independently selected from the group consisting of alkyl, aryl, alkenyl, alkynyl, cycloalkyl, heteroaryl, heterocyclyl, halo, —$NH_2$, —CN, —$NO_2$, —C(=O)OH, —C(=O)O$R_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_9$ or —$NR_9S(O_2)R_8$, wherein the alkyl, aryl, alkenyl, alkynyl, cycloalkyl, heteroaryl and heterocyclyl may each be optionally substituted with one or more $R_6$'s particularly 1-5 $R_6$'s);

$R_{4b}$, at each occurrence, is independently selected from the group consisting of hydrogen, alkyl, haloalkyl, aryl, alkenyl, alkynyl, cycloalkyl, heteroaryl, heterocyclyl, halo, —$NH_2$, —CN, —$NO_2$, —C(=O)OH, —C(=O)O$R_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_9$ and —$NR_9S(O_2)R_8$, wherein the alkyl, aryl, alkenyl, alkynyl, cycloalkyl, heteroaryl and heterocyclyl may each be optionally substituted with one or more $R_6$'s (particularly 1-5 $R_6$'s);

$R_5$ is selected from the group consisting of alkyl, aryl, cycloalkyl, heteroaryl and heterocyclyl, each of which may optionally be substituted with one or more $R_6$'s (particularly 1-5 $R_6$'s);

$R_6$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)O$R_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_8$ and —$NR_9S(O_2)R_8$;

$R_8$, at each occurrence, is independently selected from the group consisting of alkyl, aryl, cycloalkyl, heteroaryl and heterocyclyl;

$R_9$, at each occurrence, is independently selected from the group consisting of hydrogen, alkyl, alkoxy, cycloalkyl, aryl, arylalkyl, heteroaryl, heteroarylalkyl, heterocyclyl and heterocyclylalkyl, wherein the aryl, arylalkyl, heteroaryl, heteroarylalkyl, heterocyclyl or heterocyclylalkyl may each be optionally substituted with 0-5 $R_{9a}$, and the heteroaryl, heteroarylalkyl, heterocyclyl and heterocyclylalkyl each contain 1-4 heteroatoms selected from N, O and S;

$R_{9a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)O$R_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}C$(=O)$OR_{10}$, —$S(O)_2NR_{14}C$(=O)$NR_{14}R_{14}$, —C(=O)$NR_{14}S(O)_2CF_3$, —C(=O)$R_{14}$, —$NR_{14}C$(=O)H, —$NR_{14}C$(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C$(=O)$OR_8$, —$NR_{14}S(O_2)R_8$ and arylalkyl;

$R_{10}$, at each occurrence, is independently selected from the group consisting of alkyl, cycloalkyl, alkenyl, alkynyl, aryl, arylalkyl, heteroaryl, heteroarylalkyl, heterocyclyl and heterocyclylalkyl, wherein the aryl, arylalkyl, heterocyclyl or heterocyclylalkyl may each be optionally substituted with 0-5 $R_{10a}$, and the heterocyclyl and heterocyclylalkyl each contain 1-4 heteroatoms selected from N, O and S;

$R_{10a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)O$R_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_9$, —$S(O)_2NR_{14}C$(=O)$OR_9$, —$S(O)_2NR_{14}C$(=O)$NR_{14}R_{14}$, —C(=O)$NR_{14}S(O)_2CF_3$, —C(=O)$R_{14}$, —$NR_{14}C$(=O)H, —$NR_{14}C$(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C$(=O)$OR_8$, —$NR_{14}S(O_2)R_8$ and arylalkyl; and $R_{14}$, at each occurrence, is independently selected from the group consisting of hydrogen, alkyl, cycloalkyl and aryl.

In a first particular embodiment, compounds of Formula I are provided wherein A and D are each independently $CR_{4b}$ or N and B is $CR_{4b}$, provided that at least one of A and D is N.

In a second particular embodiment, compounds of Formula I are provided wherein A and D are each independently $CR_{4b}$ or N and B is $CR_{4b}$, provided that at least one of A and D is N, and E is N, O or CH.

In a third particular embodiment, compounds of Formula I are provided wherein A and D are each N and B is $CR_{4b}$.

In a fourth particular embodiment, compounds of Formula I are provided wherein A and D are each N, B is $CR_{4b}$ and E is N, O or CH.

In a fifth embodiment, compounds of Formula I are provided wherein A is N, and B and D are each $CR_{4b}$.

In a sixth particular another embodiment, compounds of Formula I are provided wherein A is N, B and D are each $CR_{4b}$ and E is N, O or CH.

In a seventh particular embodiment, compounds of Formula I are provided wherein G is N.

In an eighth particular embodiment, compounds of Formula I are provided wherein $R_{4b}$ is hydrogen.

In a ninth particular embodiment, compounds of Formula I are provided wherein:

$J$ is $CR_9R_9$, $CR_9$, $C=O$ or $N$;

the dashed line represents an optional double bond, provided that J is not $C=O$ or $CR_9R_9$ when a double bond is present;

$Y$ is $-NR_3$, O or S;

$n_2$ and $n_3$ are independently 1 or 2;

$n_4$ is 0-3;

$R_1$ is aryl or heteroaryl, each of which may be optionally substituted with one or more substituents selected from $R_4$;

$R_2$ is cycloalkyl, aryl, heteroaryl, heterocyclyl, $-C(=O)R_5$ or $-C(=O)OR_5$, wherein the cycloalkyl, aryl, heteroaryl or heterocyclyl may be optionally substituted with one or more $R_6$'s;

$R_3$ is hydrogen, alkyl or cycloalkyl;

$R_4$, at each occurrence, is independently selected from the group consisting of C1-6 alkyl, C1-4 haloalkyl, C6-10 aryl, C3-6 cycloalkyl, heteroaryl, heterocyclyl, halo, $-CN$, $-C(=O)OH$, $-C(=O)OR_{10}$, $-OCF_3$, $-OR_{10}$, $-OH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, alkyl, haloalkyl, cycloalkyl, halo, CN, $-OH$, $-OR_{10}$, $-SR_{10}$, aryl, heteroaryl and heterocyclyl, wherein the alkyl, cycloalkyl, aryl, heteroaryl and heterocyclyl may each be optionally substituted with one or more $R_6$'s;

$R_5$ is selected from the group consisting of alkyl, aryl, cycloalkyl, heteroaryl and heterocyclyl, each of which may optionally be substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, $-CN$, $-C(=O)OH$, $-C(=O)OR_{10}$, $-OCF_3$, $-OR_{10}$, $-OH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$;

$R_8$, at each occurrence, is independently selected from the group consisting of alkyl, aryl, cycloalkyl, heteroaryl and heterocyclyl;

$R_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may optionally be substituted with 0-5 $R_{9a}$, and the heteroaryl and heterocyclyl each contain 1-4 heteroatoms selected from N, O and S;

$R_{9a}$, at each occurrence, is independently selected from the group consisting of C1-6 alkyl, C1-4 haloalkyl, C6-10 aryl, C3-6 cycloalkyl, heteroaryl, heterocyclyl, halo, $-NH_2$, $-CN$, $-C(=O)OH$, $-C(=O)OR_{14}$, $-OCF_3$, $-OR_{14}$ and $-OH$;

$R_{10}$, at each occurrence, is independently selected from the group consisting of alkyl, cycloalkyl, aryl, heteroaryl and heterocyclyl, wherein the aryl, heteroaryl and heterocyclyl may each be optionally substituted with 0-5 $R_{10a}$, and the heteroaryl and heterocyclyl each contains 1-4 heteroatoms selected from N, O and S;

$R_{10a}$, at each occurrence, is independently selected from C1-6 alkyl, C1-4 haloalkyl, C6-10 aryl, C3-6 cycloalkyl, heteroaryl, heterocyclyl, halo, $-NH_2$, $-CN$, $-C(=O)OH$, $-C(=O)OR_{14}$, $-OCF_3$, $-OR_{14}$, and $-OH$; and $R_{14}$, at each occurrence, is independently selected from hydrogen, C1-6 alkyl, C3-6 cycloalkyl or C6-10 aryl.

In a tenth particular embodiment, compounds of Formula I are provided wherein:

$J$ is $CR_9R_9$, $CR_9$, $C=O$, or $N$;

the dashed line represents an optional double bond, provided that J is not $C=O$ or $CR_9R_9$ when a double bond is present;

$Y$ is $-NR_3$, O or S;

$n_2$ and $n_3$ are each independently 1 or 2;

$n_4$ is 0-3;

$R_1$ is aryl or heteroaryl, each of which may be optionally substituted with one or more substituents selected from $R_4$;

$R_2$ is selected from the group consisting of aryl, heteroaryl, heterocyclyl, $-C(=O)R_5$ and $-C(=O)OR_5$, wherein the aryl, heteroaryl and heterocyclyl may each be optionally substituted with one or more $R_6$'s;

$R_3$ is hydrogen or alkyl;

$R_4$, at each occurrence, is independently selected from the group consisting of C1-6 alkyl, C1-4 haloalkyl, C6-10 aryl, C3-6 cycloalkyl, heteroaryl, heterocyclyl, halo, $-CN$, $-C(=O)OH$, $-CO(O)OR_{10}$, $-OCF_3$, $-OR_{10}$, $-OH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl, C1-4 haloalkyl, C6-10 aryl, C3-6 cycloalkyl, halo, CN, $-OH$, $-OR_{10}$ and $-SR_{10}$, wherein the alkyl, cycloalkyl, and aryl may each be optionally substituted with one or more $R_6$'s;

$R_5$ is selected from the group consisting of C1-6 alkyl, C6-19 aryl, C3-6 cycloalkyl, heteroaryl and heterocyclyl, each of which may optionally be substituted with one or more $R_6$'s;

$R_6$, at each occurrence, is independently selected from the group consisting of C1-6 alkyl C1-4 haloalkyl, C6-10 aryl, C3-6 cycloalkyl, heteroaryl, heterocyclyl, halo, $-CN$, $-C(=O)OH$, $-C(=O)OR_{10}$, $-OCF_3$, $-OR_{10}$, $-OH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$;

$R_8$, at each occurrence, is independently selected from the group consisting of C1-6 alkyl, C6-10 aryl, C3-6 cycloalkyl, heteroaryl and heterocyclyl;

$R_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may each be optionally substituted with 0-5 $R_{9a}$, and the heteroaryl and heterocyclyl each contain 1-4 heteroatoms selected from N, O and S;

$R_{9a}$, at each occurrence, is independently selected from the group consisting of C1-6 alkyl, halo, —$NH_2$, —CN, —C(=O)OH, —C(=O)$R_{14}$, —$OCF_3$, —$OR_{14}$ and —OH;

$R_{10}$, at each occurrence, is independently selected from the group consisting of C1-6 alkyl, C3-6 cycloalkyl, C6-10 aryl, heteroaryl and heterocyclyl, wherein the aryl, heteroaryl and heterocyclyl may each be optionally substituted with 0-5 $R_{10a}$, and the heteroaryl and heterocyclyl each contains 1-4 heteroatoms selected from N, O and S;

$R_{10a}$, at each occurrence, is independently selected from the group consisting of C1-6 alkyl, halo, —$NH_2$, —CN, —C(O)OH, —C(=O)$R_{14}$, —$OCF_3$, —$OR_{14}$ and —OH; and $R_{14}$, at each occurrence, is independently selected from the group consisting of hydrogen, C1-6 alkyl and C6-10 aryl.

In an eleventh embodiment, compounds of Formula I are provided wherein:

J is $CR_9R_9$, $CR_9$, C=O or N;

the dashed line represents an optional double bond, provided that J is not C=O or $CR_9R_9$ when a double bond is present;

Y is —$NR_3$, O or S;

$n_2$ and $n_3$ are each independently 1 or 2;

$n_4$ is 0 or 2;

$R_1$ is C6-10 aryl or heteroaryl, each of which may be optionally substituted with one or more substituents selected from $R_4$;

$R_2$ is selected from the group consisting of C6-10 aryl, heteroaryl, C(=O)$R_5$ and —C(=O)$OR_5$, wherein the aryl and heteroaryl may each be optionally substituted with one or more $R_6$'s;

$R_3$ is hydrogen or C1-4 alkyl;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$R_{10}$, —$OCF_3$, —$OR_{10}$, —OH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(CO)$R_{10}$, —$NR_9C(=O)H$, —$NR_9C(=O)R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C(=O)R_8$ and —$NR_9S(O_2)R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl, C1-4 haloalkyl, C6-10 aryl, C3-6 cycloalkyl, halo, CN, —OH, —$OR_{10}$ and —$SR_{10}$, wherein the alkyl, cycloalkyl and aryl may each be optionally substituted with one or more $R_6$'s;

$R_5$ is selected from the group consisting of C1-6 alkyl, C6-10 aryl, C3-6 cycloalkyl and heteroaryl each of which may optionally be substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$R_{10}$, —$OCF_3$, —$OR_{10}$, —OH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(O)$NR_9S(O)_2CF_3$, —C(=O)$R_{10}$, —$NR_9C(=O)H$, —$NR_9C(=O)R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C(=O)OR_8$ and —$NR_9S(O_2)R_8$;

$R_8$, at each occurrence, is independently selected from the group consisting of C1-6 alkyl, C6-10 aryl, C3-6 cycloalkyl and heteroaryl;

$R_9$, at each occurrence, is independently selected from the group consisting of hydrogen, C1-6 alkyl, C3-6 cycloalkyl, C6-10 aryl and or heteroaryl, wherein the aryl and heteroaryl may each be optionally substituted with 0-5 $R_{9a}$, and the heteroaryl contains 1-4 heteroatoms selected from N, O and S;

$R_{9a}$, at each occurrence, is independently selected from the group consisting of C1-6 alkyl, halo, —$NH_2$, —CN, —C(=O)OH, —C(=O)$R_{14}$, —$OCF_3$, —$OR_{14}$ and —OH;

$R_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 $R_{10a}$, and the heteroaryl contains 1-4 heteroatoms selected from N, O and S;

$R_{10a}$, at each occurrence, is independently selected from the group consisting of C1-6 alkyl, halo, —$NH_2$, —CN, —C(=O)OH, —C(=O)$R_{14}$, —$OCF_3$, —$OR_{14}$ and —OH; and $R_{14}$, at each occurrence, is independently selected from the group consisting of hydrogen, C1-6 alkyl and C6-10 aryl.

In a twelfth embodiment, compounds of Formula I are provided wherein:

J is $CR_9$ or N;

the dashed line represents a double bond;

Y is —$NR_3$, O or S;

$n_2$ and $n_3$ are independently 1 or 2;

$n_4$ is 0 or 2;

$R_1$ is C6-10 aryl or heteroaryl, each of which may be optionally substituted with one or more substituents selected from $R_4$;

$R_2$ is heteroaryl, —C(=O)$R_5$ or —C(=O)$OR_5$, wherein the heteroaryl may be optionally substituted with one or more $R_6$'s;

$R_3$ is hydrogen;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —$NO_2$, —C(=O)OH, —C(=O)$R_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(O)$R_{10}$, —$NR_9C(=O)H$, —$NR_9C(=O)R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C(=O)R_8$ and —$NR_9S(O_2)R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl, C6-10 aryl and C3-6 cycloalkyl, wherein the alkyl, cycloalkyl, and aryl may each be optionally substituted with one or more $R_6$'s;

$R_5$ is selected from the group consisting of C1-6 alkyl, C6-10 aryl and C3-6 cycloalkyl, each of which may optionally be substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(O)OR$_8$ or —NR$_9$S(O$_2$)R$_8$;

$R_8$, at each occurrence, is independently selected from the group consisting of C1-6 alkyl and C6-10 aryl;

$R_9$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 $R_{9a}$, and the heteroaryl contains 1-4 heteroatoms selected from N, O and S;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

$R_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 $R_{10a}$, and the heteroaryl contains 1-4 heteroatoms selected from N, O and S;

$R_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and $R_{14}$, at each occurrence, is independently selected from the group consisting of hydrogen, C1-6 alkyl and C6-10 aryl.

In a thirteenth particular embodiment, compounds of formula I are provided wherein:

J is CR$_9$ or N;

the dashed line represents a double bond;

Y is —NR$_3$, O or S;

$n_2$ and $n_3$ are independently 1 or 2;

$n_4$ is 0;

$R_1$ is C6-10 aryl or heteroaryl, each of which may be optionally substituted with one or more substituents selected from $R_4$;

$R_2$ is heteroaryl, —C(=O)R$_5$ or —C(=O)OR$_5$, wherein the heteroaryl may be optionally substituted with one or more $R_6$'s;

$R_3$ is hydrogen;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —ON, —C(O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may be each optionally substituted with one or more $R_6$'s;

$R_{4b}$, at each occurrence, is independently selected from the group consisting of hydrogen, C1-6 alkyl and C3-6 cycloalkyl, wherein the alkyl and cycloalkyl may each be optionally substituted with one or more $R_6$'s;

$R_5$ is C1-6 alkyl, C6-10 aryl or C3-6 cycloalkyl, each of which may be optionally substituted with one or more $R_6$'s;

$R_6$, at each occurrence, is independently selected from the group consisting of C1-6 alkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently C1-6 alkyl or C6-10 aryl;

$R_9$, at each occurrence, is independently selected from the group consisting of hydrogen, C1-6 alkyl, C3-6 cycloalkyl and C6-10 aryl, wherein the aryl may be optionally substituted with 0-5 $R_{9a}$;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and OH;

$R_{10}$, at each occurrence, is independently hydrogen, C1-6 alkyl, C3-6 cycloalkyl or C6-10 aryl, wherein the aryl may optionally be substituted with 0-5 $R_{10a}$;

$R_{10a}$, at each occurrence, is independently selected from the group consisting of C1-6 alkyl, halo, —NH$_2$, —CN, —C(=O)OH, —(=O)OR$_{14}$, —OCF$_3$, —OR$_{14}$ and —OH; and $R_{14}$, at each occurrence, is independently hydrogen, C1-6 alkyl or C6-10 aryl.

In a fourteenth particular embodiment, compounds of Formula I are provided wherein:

A and D are independently CH or N, provided that at least one of A and D is N;

B is CH;

E is CH or N;

G is CH or N;

J is CR$_9$ or N;

the dashed line is a double bond;

Y is —NR$_3$ or O;

$n_2$ and $n_3$ are each 1;

$n_4$ is 0;

$R_1$ is phenyl or heteroaryl, each of which may be optionally substituted with one or more substituents selected from $R_4$;

$R_2$ is heteroaryl, —C(=O)R$_5$ or —C(=O)OR$_5$, wherein the heteroaryl may be optionally substituted with one or more $R_6$'s;

$R_3$ is hydrogen;

$R_4$, at each occurrence, is independently selected from the group consisting of C1-6 alkyl, C1-4 haloalkyl, C3-6 cycloalkyl, phenyl, heteroaryl, halo, —NH$_2$, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, phenyl, or heteroaryl may each be optionally substituted with one or more (for example, 1-5) $R_6$'s;

$R_5$ is C1-6 alkyl, C3-6 cycloalkyl or phenyl, each of which may optionally be substituted with one or more (for example, 1-5) $R_6$'s;

$R_6$, at each occurrence, is independently selected from the group consisting of C1-6 alkyl, C1-4 haloalkyl, phenyl, heteroaryl, halo, —NH$_2$, —CN, —C(=O)OH, —C(=O)OR$_{10}$, —OCF$_3$—OR$_{10}$, —OH, —SR$_{10}$, —C(O)NR$_9$R$_9$, —NR$_9$R$_9$, —S(O)$_7$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently C1-6 alkyl or phenyl;

$R_9$, at each occurrence, is independently hydrogen, C1-6 alkyl, C3-6 cycloalkyl or phenyl, wherein the phenyl may be optionally substituted with 0-5 $R_{9a}$;

$R_{9a}$, at each occurrence, is independently selected from the group consisting of C1-6 alkyl, halo, —$NH_2$, —CN, —C(=O)OH, —C(=O)O$R_{14}$, —O$CF_3$, —O$R_{14}$ and —OH;

$R_{10}$, at each occurrence, is independently hydrogen, C1-6 alkyl, C3-6 cycloalkyl or phenyl, wherein the phenyl may be optionally substituted with 0-5 $R_{10a}$;

$R_{10a}$, at each occurrence, is independently selected from the group consisting of C1-6 alkyl, halo, —$NH_2$, —CN, —C(=O)OH, —C(=O)O$R_{14}$, —O$CF_3$, —O$R_{14}$ and —OH; and $R_{14}$, at each occurrence, is independently hydrogen, C1-6 alkyl or phenyl.

In a fifteenth particular embodiment, compounds of Formula I are provided wherein:

A and D are independently CH or N, provided that at least one of A and D is N;

B is CH;

E is CH or N (more particularly, N);

G is N;

J is $CR_9$ or N;

the dashed line is a double bond;

Y is —$NR_3$ or O;

$n_2$ and $n_3$ are 1;

$n_4$ is 0;

$R_1$ is phenyl, pyridyl or pyrimidinyl, each of which may be optionally substituted with one or more substituents selected from $R_4$;

$R_2$ is pyrimidinyl, pyridyl, oxadiazolyl, benzoxazole or C(=O)O$R_5$, wherein the heteroaryl may be optionally substituted with one or more (for example, 1-5) $R_6$'s;

$R_3$ is hydrogen;

$R_4$, at each occurrence, is independently selected from the group consisting of C1-6 alkyl, C1-4 haloalkyl, C3-6 cycloalkyl, phenyl, heteroaryl, halo, —$NH_2$, —CN, —C(=O)OH, —C(=O)O$R_{10}$, —O$CF_3$, —O$R_{10}$, —OH, —S$R_{10}$, —C(=O)$NR_9R_9$, —$NR_9R_9$, —S(O)$_2NR_9R_9$, —C(=O)$NR_9$S(O)$_2R_9$, —S(O)$_2NR_9$C(=O)O$R_9$, —C(=O)$R_{10}$, —$NR_9$C(=O)H, —$NR_9$C(=O)$R_{10}$, —OC(=O)$NR_9R_9$, —S(=O)$R_{10}$, —S(O)$_2R_{10}$, —$NR_9$C(=O)O$R_8$ and —$NR_9$S(O$_2$)$R_8$, wherein the alkyl, phenyl and heteroaryl may each be optionally substituted with one or more (for example, 1-5) $R_6$'s;

$R_5$ is C1-6 alkyl, C3-6 cycloalkyl or phenyl, each of which may be optionally substituted with one or more (for example, 1-5) $R_6$'s;

$R_6$, at each occurrence, is independently selected from the group consisting of C1-6 alkyl, C1-4 haloalkyl, C3-6 cycloalkyl, phenyl, heteroaryl, halo, —$NH_2$, —CN, —C(=O)OH, —C(=O)O$R_{10}$, —O$CF_3$, —O$R_{10}$, —OH, —S$R_{10}$, —C(=O)$NR_9R_9$, —$NR_9R_9$, —S(O)$_2NR_9R_9$, —C(=O)$NR_9$S(O)$_2R_9$, —S(O)$_2NR_9$C(=O)O$R_9$, —C(=O)$R_{10}$, —$NR_9$C(=O)H, —$NR_9$C(CO)$R_{10}$, —OC(=O)$NR_9R_9$, —S(=O)$R_{10}$, —S(O)$_2R_{10}$, —$NR_9$C(=O)O$R_8$ and —$NR_9$S(O$_2$)$R_8$;

$R_8$, at each occurrence, is independently C1-6 alkyl or phenyl;

$R_9$, at each occurrence, is independently hydrogen, C1-6 alkyl, C3-6 cycloalkyl or phenyl, wherein the phenyl may optionally be substituted with 0-5 $R_{9a}$;

$R_{9a}$, at each occurrence, is independently selected from the group consisting of C1-6 alkyl, halo, —$NH_2$, —CN, —C(O)OH, —C(O)O$R_{14}$, —O$CF_3$, —O$R_{14}$ and —OH;

$R_{10}$, at each occurrence, is independently C1-6 alkyl, C3-6 cycloalkyl or phenyl, wherein the phenyl may optionally be substituted with 0-5 $R_{10a}$;

$R_{10a}$, at each occurrence, is independently selected from the group consisting of C1-6 alkyl, halo, —$NH_2$, —CN, —C(=O)OH, —C(=O)O$R_{14}$, —O$CF_3$, —O$R_{14}$ and —OH; and $R_{14}$, at each occurrence, is independently hydrogen or C1-6 alkyl.

In a sixteenth particular embodiment, compounds of formula I are provided wherein the compound is a compound of Formula Ia:

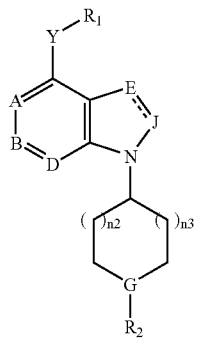

Formula Ia

Further subgroups of Formula Ia comprise a subset of each particular embodiment listed herein (for example, embodiments 1-15 and 17-26, but limited to where $n_4$=0).

For the general description of the invention and as well as for each of the embodiments 1-26 described herein, more particular values are as follows:

"C6-10 aryl" has a more particular value of phenyl.

"Heteroaryl" has a more particular value (especially for $R_4$ and $R_6$) of a single ring with 6 atoms of which 1-4 and, even more particularly 1-3, atoms are each independently selected from O, S and N and the remainder are selected to be carbons. Even more particular values for heteroaryl are oxazole, triazole, imidazole and pyrazole.

"One or more $R_6$'s" has a more particular value of 1-5 of $R_6$'s which are independently selected from the listed definition for $R_6$ for that embodiment.

"Heterocyclyl" has a more particular value as comprising 1-4 atoms selected from N, O and S, with the remaining atoms being carbond, and an even more particular value as a 4- to 6-membered ring with 1-2 members selected from O, S and N and the remaining atoms being carbon.

"One or more substituents selected from $R_4$" has a more particular value of 1-5 of $R_4$.

In a seventeenth particular embodiment, compounds of the present invention are selected from the compounds exemplified in the examples.

In an eighteenth particular embodiment, the present invention relates to pharmaceutical compositions comprised of a therapeutically effective amount of a compound of the present invention, alone or, optionally, in combination with a pharmaceutically acceptable carrier and/or one or more other agent(s), for example, a glucagon-like peptide-1 receptor agonist or fragment thereof.

In a nineteenth particular embodiment, the present invention relates to methods of modulating the activity of the GPR119 G protein-coupled receptor comprising administering to a mammalian patient, for example, a human patient, in need thereof a therapeutically effective amount of a compound of the present invention, alone, or optionally, in combination with another compound of the present invention and/or at least one other type of therapeutic agent.

In a twentieth particular embodiment, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In a twenty-first particular embodiment, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-second particular embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-third particular embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-fourth particular embodiment, the present invention relates to a method for preventing, modulating, or treating the progression or onset of obesity comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-fifth particular embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-sixth particular embodiment, the present invention relates to a method for preventing, modulating, or treating the progression or onset of hypertension comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

This Definition section is listed for convenience, but is subject to the specific and narrower definitions given for the embodiments and Examples listed elsewhere in the specification and the Examples.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, $C=N$ double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Steven D. Young, S. D. et al., *Antimicrobial Agents and Chemotherapy*, 2602-2605 (1995).

To the extent that compounds of the formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

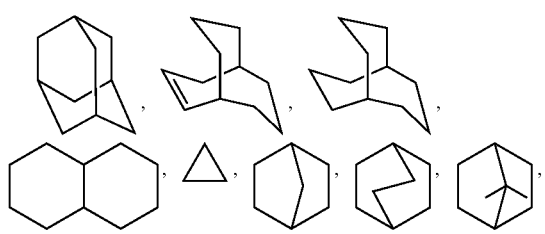

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $-C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings
for example

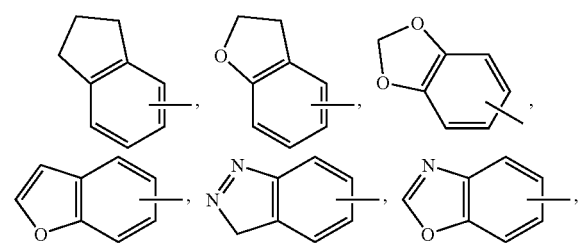

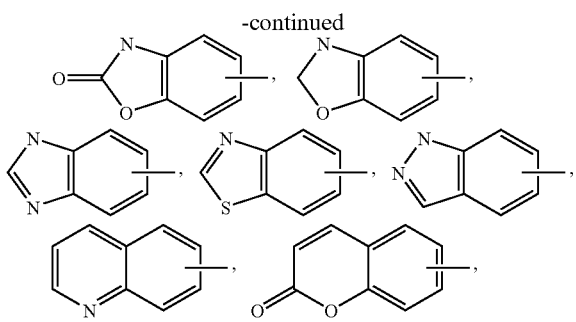

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyd aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizin-yl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.
The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry*, Camille G. Wermuth et al., Ch. 31 (Academic Press, 1996);
b) *Design of Prodrugs*, edited by H. Bundgaard (Elsevier, 1985);
c) *A Textbook of Drug Design and Development*, P. Krogsgaard-Larson and H. Bundgaard, eds. Ch. 5, pp. 113-191 (Harwood Academic Publishers, 1991); and
d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders. As used in this invention a therapeutically effective amount is believed to be in the range of 0.1-100 mg/kg per day.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

The synthesis routes described in the following schemes are for simplicity shown for compounds of formula I where G is N or CH, $n_2$ and $n_3$ are 1, and $n_4$ is 0, such that the synthesis is described for those compounds of formula I containing a piperidine or cyclohexane ring. It will be recognized by those skilled in the art that the synthesis routes described in the following schemes can also be readily applied to those compounds of formula I where G is N or CH, $n_2$ and $n_3$ are independently 0-2, and $n_4$ is 0-3. It will be further recognized that the appropriate starting materials for those compounds of formula I where G is N or CH, $n_2$ and $n_3$ are independently 0-2, and $n_4$ is 0-3 are either commercially available or can be readily prepared by standard procedures known to those skilled in the art.

The synthesis of compounds of Formula I where E is N or NH is described in Scheme 1. These compounds can be prepared from dichloronitro compounds (1) which are either commercially available or can be readily prepared by one skilled in the art. For example, 4,6-dichloro-5-nitropyrimidine (1, A and D are N, B is CH) is commercially available, while 2,4-dichloro-3-nitropyridine (1, A is N, B and D are CH) is readily available from 2,4-dihydroxypyridine (see Norman, M. H. et al., *J. Med. Chem.*, 43:4288 (2000)). Treatment of (1) with amine (2) in the presence of a base such as potassium carbonate or cesium carbonate, in a solvent such as DMF, THF or methylene chloride affords (3). Nitro group reduction can be accomplished with a variety of reagents, such as with $Zn/NH_4Cl$ or $SnCl_2$, or by a number of other reagents known to those skilled in the art, to provide diamine (4). Treatment of diamine (4) with a diazotizing reagent, such as sodium nitrite in acidic medium, such as acetic acid or aqueous HCl, leads to diazotization of the primary aniline and subsequent cyclization to afford the fused triazole (5). A preferred procedure involves treating (4) with sodium nitrite in glacial acetic acid at room temperature to afford (5). Treatment of (4) with a variety of reagents, such as trimethylorthoformate, N,N-dimethylformamide dimethyacetal, or formic acid (where $R_9$ is H), or with various orthoesters or carboxylic acids (where $R_9$ is alkyl or aryl) at elevated temperature, with or without a solvent such as toluene affords the fused imidazole (6). A preferred procedure when $R_9$ is hydrogen involves heating (4) in neat trimethylorthoformate at 60-100° C. to afford (6). Treatment of (4) with phosgene or a phosgene equivalent, such as triphosgene or carbonyl diimidazole, in the presence of a base such as triethylamine, in a solvent such as methylene chloride or THF, affords the fused cyclic urea (7). A preferred procedure involves treating (4) with phosgene and triethylamine in THF at room temperature to afford (7). Treatment of (5-7) with an appropriate reagent $R_1$—YH (8), where Y=$NR_3$, O or S, to afford (9) can be accomplished under a wide variety of conditions familiar to those skilled in the art. For example, when Y is $NR_3$, the reaction can be accomplished under palladium-catalyzed coupling conditions, using an appropriate palladium catalyst, such as Pd(dppf)$Cl_2$, $Pd_2(dba)_3$, $Pd(PPh_3)_4$ or $Pd(OAc)_2$, etc., and a suitable ligand such as BINAP, $PPh_3$, $P(tBu)_3$, o-(biphenyl)$P(tBu)_2$, etc., and a base such as but not limited to NaOtBu or $Cs_2CO_3$ in a suitable solvent such as DMF, toluene, THF or DME, at elevated temperatures, to yield (9) (see Yang, B. H. et al., *J. Organomet. Chem.*, 576:125 (1999) and Urgaonkar, S. et al., *J. Org. Chem.*, 68:8416 (2003), and references cited therein). In a preferred procedure, (5-7) is treated with an appropriate aniline (8) using Pd(dppf)$Cl_2$ as catalyst, BINAP as the ligand, NaOtBu as the base in toluene at 100° C., with or without microwave irradiation, to afford compounds (9). When Y is O, the reaction can be accomplished by a variety of palladium-catalyzed coupling conditions to afford diaryl ethers (9). For example, treatment of (5-7) with a phenol (8) in the presence of a palladium catalyst, such as $Pd(OAc)_2$, $Pd_2(dba)_3$, etc., a ligand such as DPPF, BINAP, $P(tBu)_3$, o-(biphenyl)$P(tBu)_2$, etc., and a base such as but not limited to $K_2CO_3$, or $K_3PO_4$ in a suitable solvent such as DMF, toluene, THF or DME, at elevated temperatures, affords ethers (9) (for a recent review of diaryl ether synthesis, see Frlan, R. et al., *Synthesis*, 2271 (2006)). Diaryl ethers (9) can also be prepared by the Ullmann coupling reaction, which involves treatment of (5-7) with a phenol (8) or its sodium salt in the presence of a copper (I) salt, such as $Cu_2O$, CuI, CuBr, $CuPF_6$ (MeCN), etc., a suitable base, such as $Cs_2CO_3$ or NaOtBu, with or without an added ligand, such as 1,10-phenanthroline, Chxn-Py-Al, $PPh_3$, etc., in a suitable solvent such as pyridine, toluene, DMF, MeCN, etc, at elevated temperatures, to afford ethers (9) (see Frlan, R. et al., *Synthesis*, 2271 (2006)). When Y is S, the reaction can also be accomplished by palladium-catalyzed coupling of (5-7) with an aryl thiol (8), for example by using $Pd_2(dba)_3$ or $Pd(OAc)_2$ as catalyst, a ligand such as Xantphos or DPEphos, a base such as Hunig's base or potassium carbonate, in dioxane or toluene as solvent at elevated temperature, to afford diaryl thioethers (9) (see Itoh, T. et al., *Org. Lett.*, 6:4587 (2004) and references therein). Alternatively, diaryl thioethers (9) can also be prepared by the Ullman coupling reaction similar to that described for diaryl ethers. For example, treatment of (5-7) with a thiophenol (8) in the presence of a copper (I) salt, such as $Cu_2O$, CuI, CuBr, CuPF$_6$(MeCN), etc., a suitable base, such as Cs$_2$CO$_3$ or NaOtBu, with or without an added ligand, such as 1,10-phenanthroline, Chxn-Py-Al, PPh$_3$, etc., in a suitable solvent such as pyridine, toluene, DMF, MeCN, etc, at elevated temperatures, affords thioethers (9). Thus, Scheme 1 provides a general route to prepare compounds of Formula I where E is N or NH.

room temperature or elevated temperature, with or without microwave irradiation, to afford (10). A preferred procedure involves treating (3) with reagent (8, Y=O) in the presence of triethylamine in THF at 50-70° C. to afford (10). Nitro group reduction can then be accomplished as previously described, using Zn/NH$_4$Cl or SnCl$_2$, or a variety of other known procedures, to afford the diamine (11). As described previously

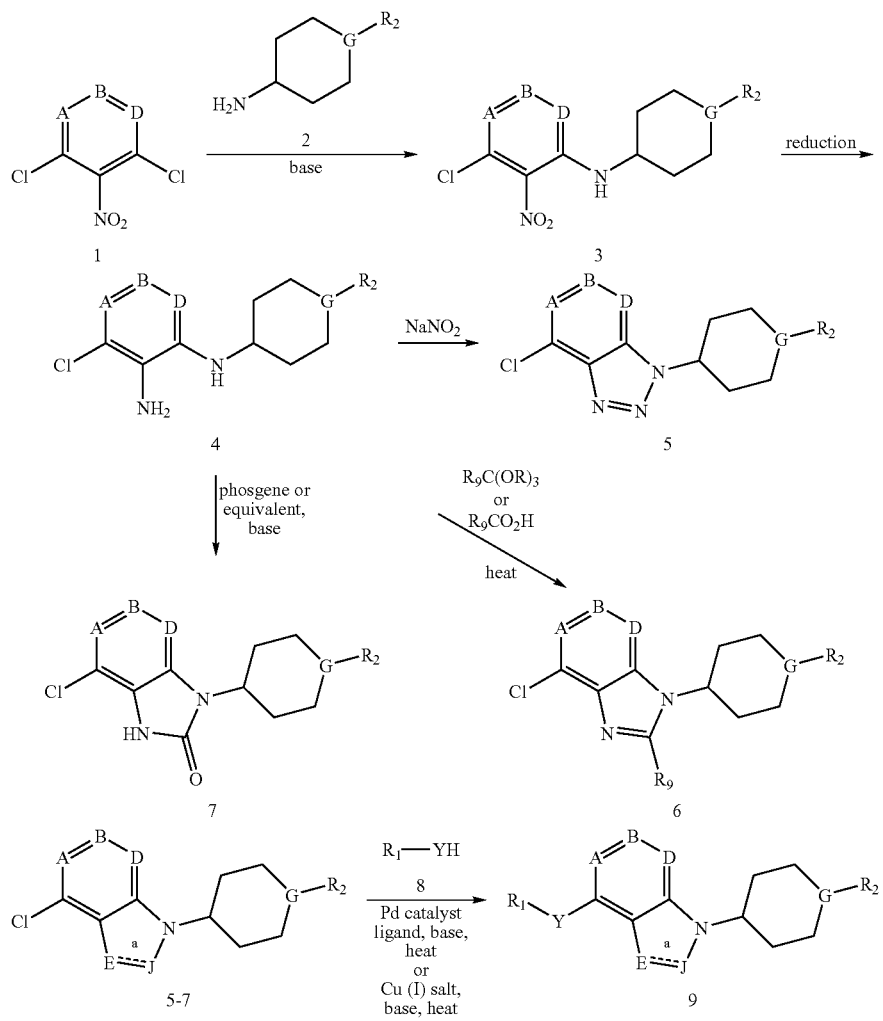

Scheme 1

An alternative preparation of these compounds where Y is O or S is shown in Scheme 2. Coupling of (3) with reagent (8) where Y is O or S can precede bicyclic ring formation, giving (10). This reaction can be readily accomplished by treatment of (3) with (8), where Y is O or S, in the presence of a base such as potassium carbonate, cesium carbonate or NaH, in a suitable solvent such as DMF, THF or methylene chloride, at in Scheme 1, bicyclic ring formation can be accomplished using sodium nitrite in acidic medium to produce triazole (12), trimethylorthoformate, N,N-dimethylformamide dimethylacetal, or formic acid to produce imidazole (13), or phosgene or a phosgene equivalent in the presence of a suitable base to afford the urea (14). Compounds (12-14) represent compounds of Formula I where E is N.

Scheme 2

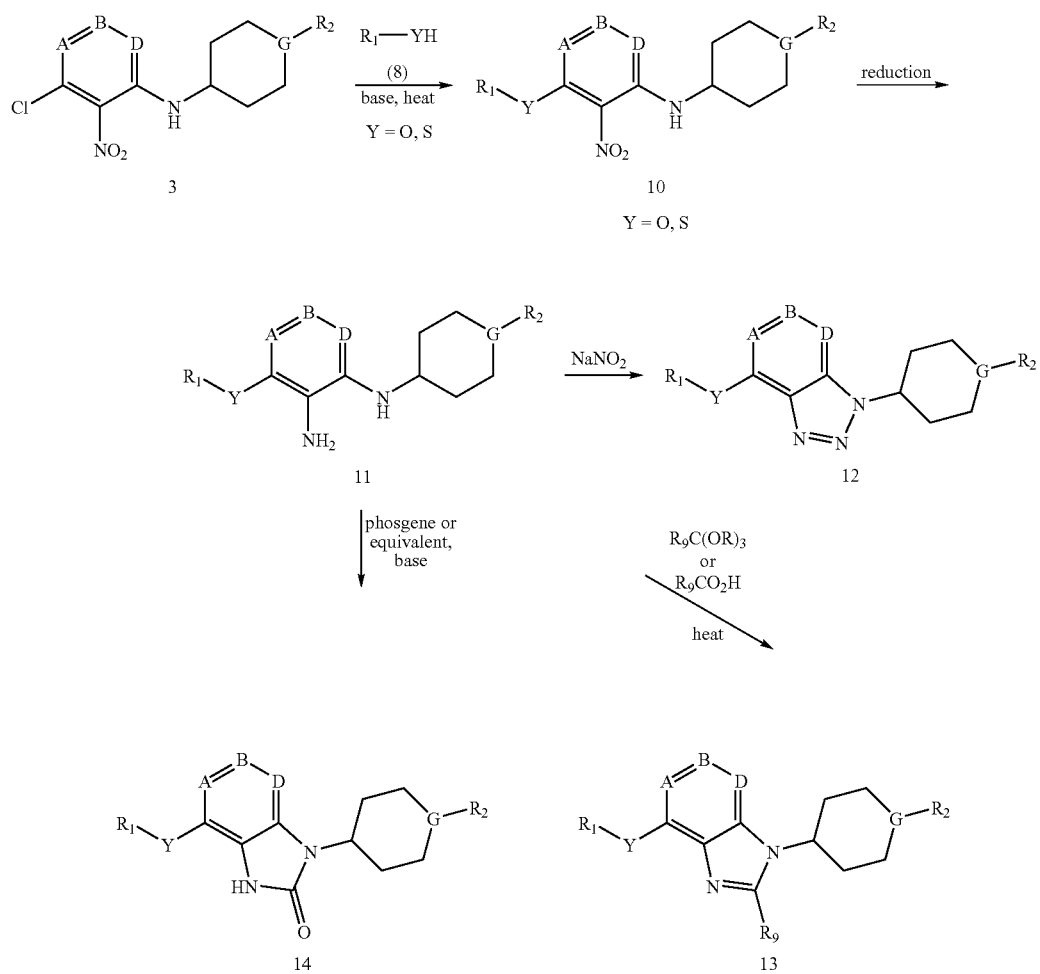

The preparation of compounds of Formula I where E is CH and J is N is described in Scheme 3. Compounds (15) are either commercially available or readily prepared by methods known to those skilled in the art. For example, 4,6-dichloro-5-formylpyrimidine (15, X is Cl, A and D are N, B is CH) is commercially available, while 2,4-dichloro-3-formylpyridine (15, X is Cl, A is N, B and D are CH) can be readily prepared from 2-4-dichloropyridine (see Radinov, R., et al., *J. Org. Chem.*, 56:4793 (1991)). Treatment of (15) with a protected hydrazine (16), in the presence of a base such as but not limited to triethylamine, potassium carbonate or cesium carbonate, in a solvent such as THF, methylene chloride or DMF, affords compound (19). The hydrazine (16) can be prepared from the corresponding ketone (17) and an appropriate monoprotected hydrazine (18), such as, but not limited to, t-butyl carbazate when PG is BOC. Thus, condensation of (17) with (18) under dehydrating conditions, such as for example by refluxing in toluene, affords a hydrazone intermediate, which can be reduced by a variety of reagents, such as but not limited to sodium borohydride, sodium triacetoxyborohydride, or sodium cyanoborohydride. Removal of the protecting group PG from (19) is readily accomplished, for example when PG is BOC, this reaction can be accomplished by using HCl in solvents such as ether, THF or dioxane, or by using trifluoroacetic acid either neat or in a solvent such as methylene chloride. It will be recognized by those skilled in the art that a wide variety of protecting groups are possible for use on hydrazine (18) and a wide variety of conditions will be available for removing various protecting groups from (19) (see Greene, T. et al., *Protecting Groups in Organic Synthesis*, John Wiley & Sons, Inc., New York, N.Y. (1991) and references therein). Removal of the protecting group from (19) will liberate a free amine, which readily condenses onto the aldehyde group, either spontaneously or under dehydrating conditions, such as by refluxing in toluene, with or without an acid catalyst such as p-toluenesulfonic acid, and removal of water with a Dean-Stark trap, affording the pyrazole fused bicyclic compounds (20). Alternatively, treatment of (15) with hydrazine with or without a base such as triethylamine, potassium carbonate or potassium hydroxide, in a solvent such as THF, methylene chloride, methanol or DMF, with or without heating, affords the pyrazole (21). Treatment of (21) with bromide or mesylate (22) in the presence of a base such as but not limited to triethylamine, potassium carbonate, sodium hydride, sodium hydroxide or cesium carbonate, in a solvent such as THF, methylene chloride or DMF, with or without microwave irradiation, affords compound (20). Treatment of compound (20) with reagent (8) under various conditions as described in Scheme 1 affords (23), which represents Formula I where E is CH and J is N.

Scheme 3

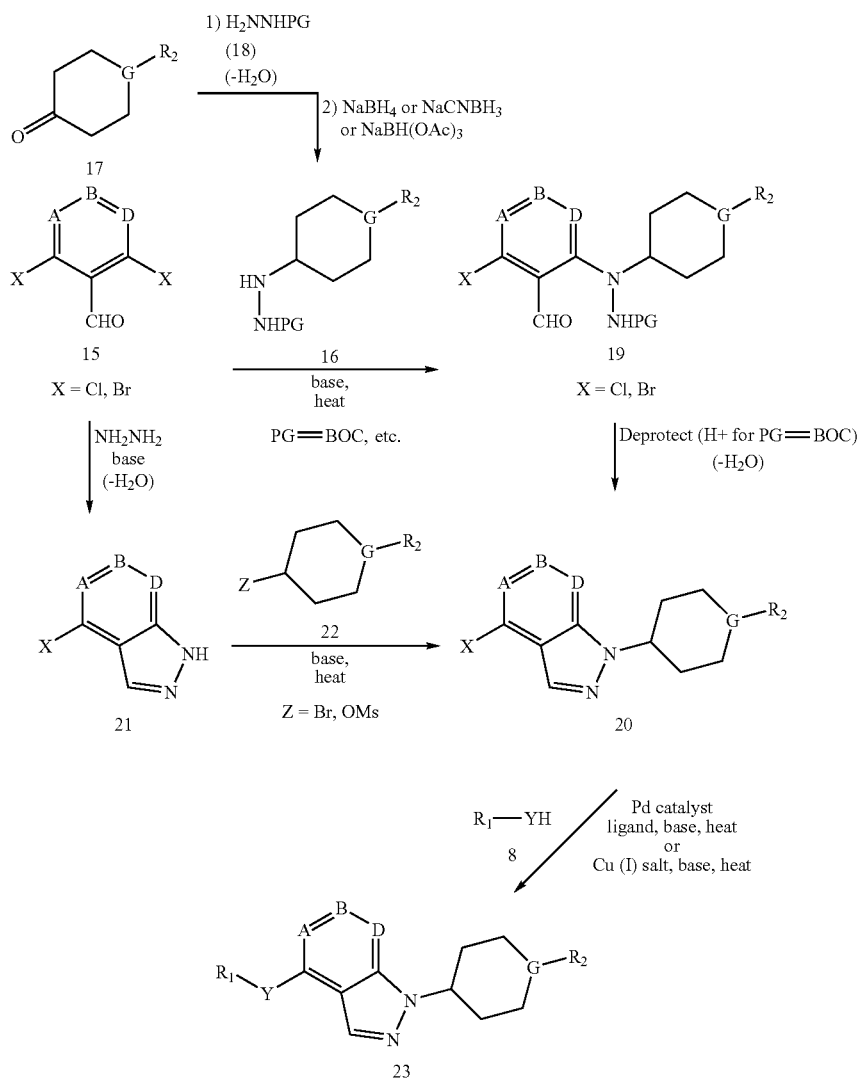

The preparation of compounds of Formula I where E is CH or CH$_2$ and J is CR$_9$ or CR$_9$R$_9$, where one R$_9$ is H, is described in Scheme 4. Treatment of (15) with amine (2) in the presence of a base such as triethylamine, potassium carbonate or cesium carbonate, in a solvent such as DMF, THF or methylene chloride affords (24). Treatment of (24) with the methoxytriphenylphosphorane reagent (25), which can be readily generated from an appropriate (methoxymethyl)triphenylphosphonium chloride by treatment with a strong base such as n-BuLi or KO-t-Bu, in a solvent such as THF or DME, affords a vinyl ether intermediate which upon mild acid hydrolysis, such as with dilute aqueous HCl or p-toluenesulfonic acid, gives a homologated aldehyde or ketone (26) (see Justus, K. et al., *Tetrahedron Lett.*, 32:5781 (1991)). Alternatively, the transformation of (24) to (26) can be accomplished by treating the aldehyde (24) sequentially with dimethylsulfonium methylide, in a solvent such as THF or DMSO, to produce an epoxide intermediate, and then with a Lewis acid such as boron trifluoride etherate in a solvent such as THF, to afford the homologated aldehyde (26, both R$_9$ are H) (see Hong, C. Y. et al., *J. Am. Chem. Soc.*, 115:11028 (1993)). Compounds (26) can undergo further condensation, either spontaneously or under dehydrating conditions, such as by refluxing in toluene, with or without an acid catalyst such as p-toluenesulfonic acid, and removal of water with a Dean-Stark trap, affording the indole-fused compound (27). Reduction of the indole (27) to the indoline (28) can be accomplished by a variety of procedures known to those skilled in the art. For example, treatment of (27) with sodium borohydride or sodium cyanoborohydride in acidic conditions, such as in the presence of trifluoroacetic acid, affords the reduced product (28) (Ketcha, D. M. et al., *Tetrahedron Lett.*, 30:6833 (1989)). Alternatively, the indole (27) can be reduced to the indoline (28) with triethylsilane in trifluoroacetic acid (Magnus, P. et al., *J. Am. Chem. Soc.*, 109:2706 (1987)). Treatment of indole (27) or indoline (28) with reagent (8) under various conditions as described in Scheme 1 affords compounds (29) and (30), respectively, which represents Formula I where E is CH or CH$_2$ and J is CR$_9$ or CR$_9$R$_9$, where one R$_9$ is H. It will be recognized by those skilled in the art that indole (29) can also be reduced to indoline (30) after coupling with reagent (8), by the procedures described above for the conversion of (27) to (28), or by catalytic hydrogenation using, for example, palladium on carbon as the catalyst in a solvent such as methanol or ethanol, or by various other procedures known to those skilled in the art.

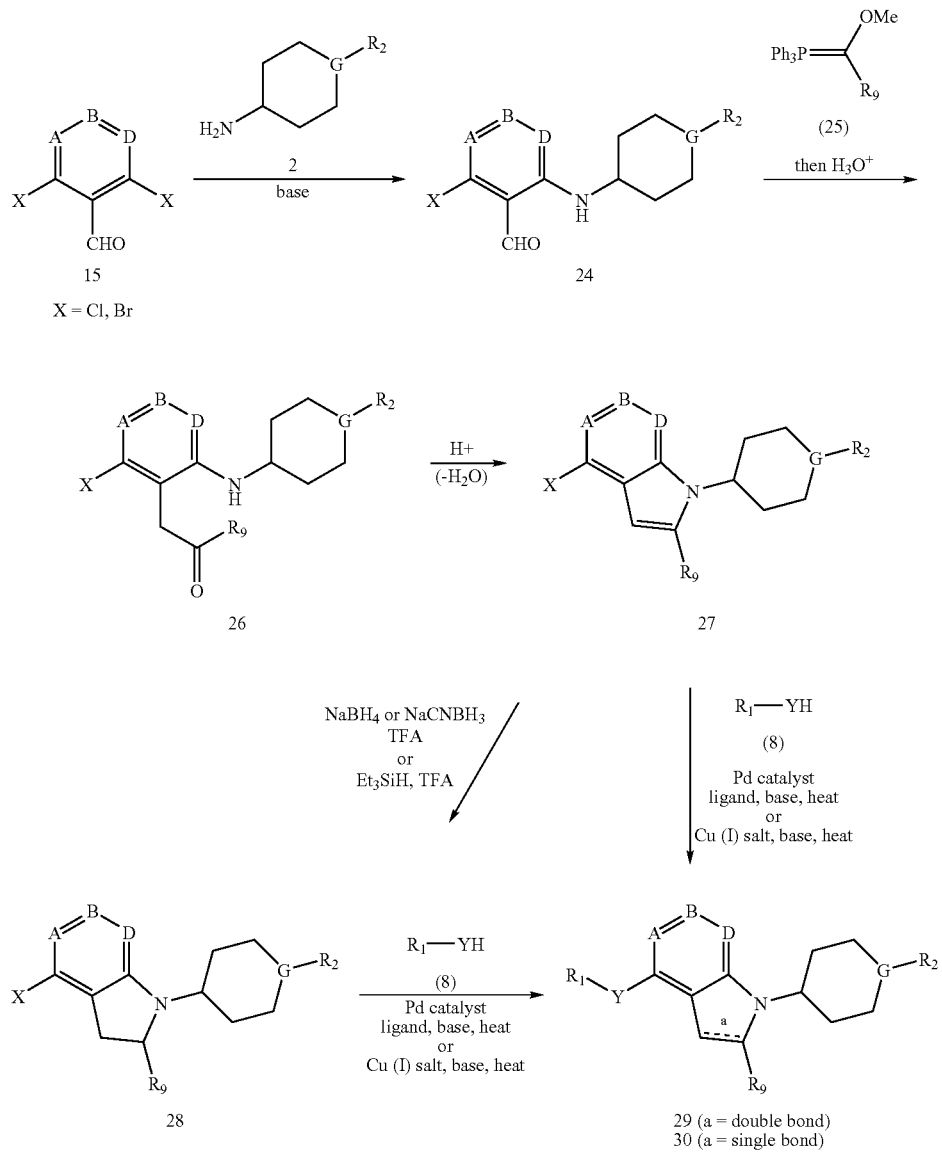

Scheme 4

A preparation of compounds of Formula I where E is CH$_2$ and J is C=O is described in Scheme 5. The aldehyde (24) can be homologated to the corresponding acid (34) or ester (35) derivative by a variety of procedures familiar to those skilled in the art (for a survey of methods, see Katritzky, A. R. et al., *Synthesis*, 1425 (1996)). For example, treatment of (24) with the anion of α-(N-methylanilino)acetonitrile (31) in a solvent such as THF, followed by acidic hydrolysis, such as dilute HCl, affords the acid derivative (34) (Takahashi, K. et al., *J. Org. Chem.*, 48:3566 (1983)). Likewise, treatment of (24) with the lithium anion of trimethylsilyl(methoxy)benzotriazol-1-ylmethane (32) in a solvent such as THF, followed by treatment with zinc (II) bromide and HCl at elevated temperature, in a solvent such as dioxane, affords the acid (34) (Katritzky, A. R. et al., *Synthesis*, 1425 (1996), and references therein). Alternatively, treatment of (24) with 2-lithio-2-(trimethylsilyl)-1,3-dithiane in a solvent such as THF, followed by mercuric (II) chloride-catalyzed methanolysis of the ketene thioacetal intermediate affords the ester (35) (Boger, D. L. et al., *J. Org. Chem.*, 49:4050 (1984), and references therein). The acid (34) and the ester (35) can undergo further condensation, either spontaneously or by heating at elevated temperature with or without an acid catalyst such as p-toluenesulfonic acid, or by heating under dehydrating conditions, such as by refluxing in toluene with removal of water by a Dean-Stark trap, with or without an acid catalyst such as p-toluenesulfonic acid, affording the lactam compound (36). Treatment of lactam (36) with reagent (8) under various conditions as described in Scheme 1 affords compounds (37), which represents Formula I where E is CH$_2$ and J is C=O.

Scheme 5

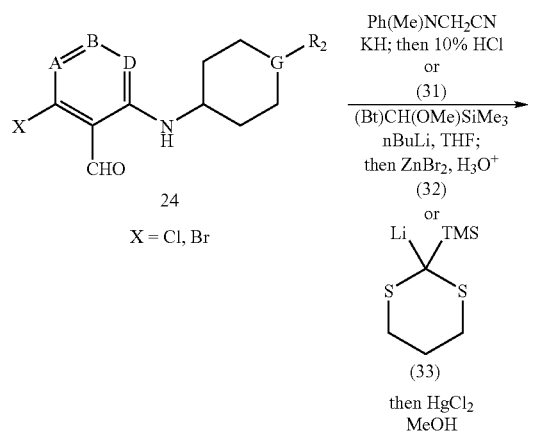

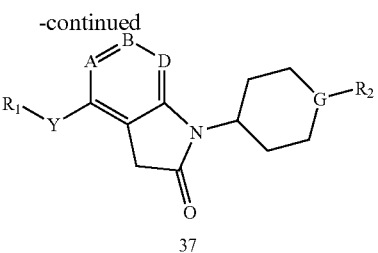

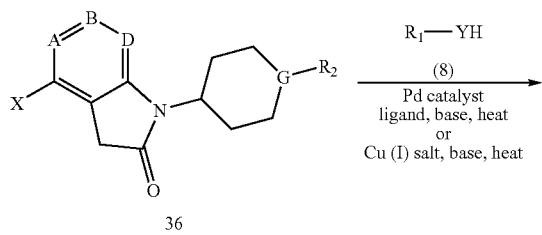

An alternative synthesis of compounds of Formula I where E is CH or $CH_2$ and J is CH, $CH_2$ or C=O is described in Scheme 6. In contrast to the methods described in Schemes 4 and 5, a more stepwise process can also be employed to accomplish the one carbon homologation of aldehyde (24). For example, a three step sequence, involving reduction of (24) by any of a variety of hydride reducing agents, such as sodium borohydride, conversion of the resulting alcohol to the corresponding bromide or mesylate, such as by treating with phosphorus tribromide or methanesulfonyl chloride and a base, such as triethylamine, respectively, followed by displacement of the bromide or mesylate with cyanide, such as by treatment with sodium cyanide or potassium cyanide in a solvent such as DMF or DMSO, affords the nitrile (38), where the aldehyde has been homologated by one carbon (see Haning, H. et al., *Bioorg. Med. Chem. Lett.*, 15:1835 (2005); Schubert, U., *Synthesis*, 364 (1978)). Reduction of the nitrile to an aldehyde can be accomplished by treatment with diisobutylaluminum hydride (DIBAL) in a solvent such as methylene chloride or THF, to afford aldehyde (26) (see Scheme 4), which can undergo condensation to provide (27) as described in Scheme 4. Reduction of (27) to afford (28) can also be accomplished as described in Scheme 4. The nitrile (38) can alternatively be hydrolyzed under acidic conditions at elevated temperature to afford the carboxylic acid (34) (see Scheme 5), which can undergo condensation to provide (36) as described in Scheme 5. The lactam derivatives (36) can be reduced to either (27) or (28) by treating with reagents such as lithium aluminum hydride, diisobutylaluminum hydride or borane (see Sirowej, H. et al., *Synthesis*, 84 (1972) and *Helv. Chim. Acta*, 73:1719 (1990) and references therein). Also, compound (27) can be oxidized to the lactam (36) by employing reagents such as dimethyldioxirane or N-bromosuccinimide (see Zhang, X. et al., *J. Am. Chem. Soc.*, 115:8867 (1993) and Deng, H. et al., *Org. Lett.*, 3:3001 (2001)). As described previously, treatment of compounds (27), (28) or (36) with reagent (8) under various conditions as described in Scheme 1 affords compounds of Formula I where E is CH or $CH_2$ and J is CH, $CH_2$ or C=O.

Scheme 6

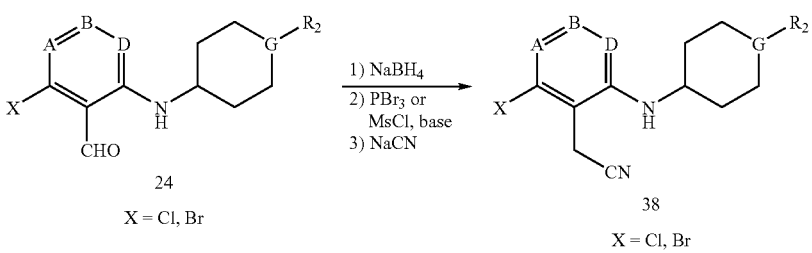

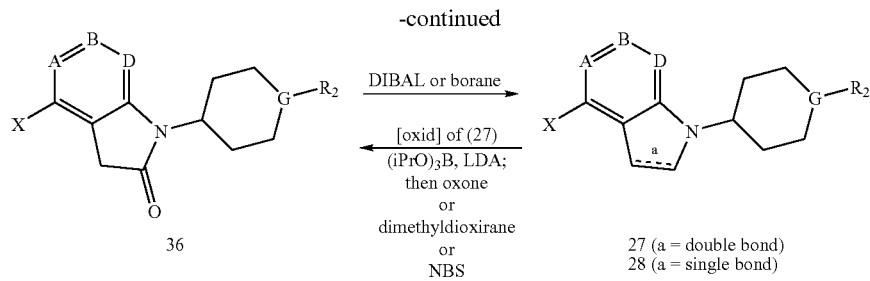

The compounds of formula I where E is O and J is C=O or $CR_9R_9$ can be prepared as described in Scheme 7. Compound (39) is readily available either from commercial sources or by procedures known to those skilled in the art. Selective nitration ortho to the alcohol with nitric acid and sulfuric acid affords nitro compound (40). For example, 2-chloro-3-hydroxypyridine (A is N, B and D are CH) is readily nitrated with nitric acid and sulfuric acid at room temperature to afford the desired nitropyridine (40) (see US2006/0155128A1). Protection of the phenol by, for example, but not limited to, methyl ether (PG=methyl) or any of a variety of trialkylsilyl groups (PG=$R_3$Si), gives (41). The methyl ether can be prepared by treating (40) with methyl iodide in the presence of a base such as sodium hydride or potassium carbonate, in a solvent such as THF or DMF. Alternatively, the methyl ether can be prepared by treating (40) with trimethylsilyldiazomethane in a solvent such as acetonitrile to afford (41, PG=methyl). The trialkylsilyl protecting group can be introduced by treating (40) with a suitable trialkylsilyl chloride or triflate in the presence of a base such as triethylamine, in a solvent such as THF or $CH_2Cl_2$. It will be recognized by those skilled in the art that additional protecting groups can be employed for phenol (40). For an excellent reference for alcohol and phenol protecting groups, see Greene, T. et al., *Protecting Groups in Organic Synthesis*, John Wiley & Sons, Inc., New York, N.Y. (1991) and references therein. For the conversion of (41) to (42) the nitro group of (41) can be reduced by a variety of reducing agents well known to those skilled in the art, such as by Zn/$NH_4Cl$ or $SnCl_2$, to afford an amino compound which can then undergo reductive amination with ketone (2) in the presence of a borohydride reducing agent, such as sodium triacetoxyborohydride. Alternatively, the amino compound can be treated with ketone (2) in the presence of an acid catalyst, such a p-toluenesulfonic acid, to form the imine upon removal of water, such as in toluene at reflux with a Dean-Stark trap. The resulting imine can then be reduced with an appropriate borohydride reducing agent, such as with sodium borohydride, in a solvent such as methanol or THF. Deprotection of (42) to liberate the phenol affords (43). When PG is methyl the deprotection can be accomplished using boron tribromide, TMSI, or other methods known to those skilled in the art, to provide the phenol (43). It will be recognized by those skilled in the art that when G is nitrogen and when $R_2$ is an acid labile protecting group, such as tert-butoxycarbonyl (BOC), deprotection under acidic conditions may also cause loss of the nitrogen protecting group. In such case (G=N, $R_2$=BOC) the nitrogen can be reprotected using di-tert-butyldicarbonate ($BOC_2O$) to afford (43). In the case of (42) where PG is trialkylsilyl, the deprotection can be accomplished using tetrabutylammonium fluoride (TBAF) in a solvent such as THF (see Greene, T. et al., *Protecting Groups in Organic Synthesis*, John Wiley & Sons, Inc., New York, N.Y. (1991) and references therein). Treatment of (43) with phosgene or a phosgene equivalent, such as triphosgene or carbonyl diimidazole, in the presence of a base such as triethylamine, in a solvent such as methylene chloride or THF, affords the fused cyclic carbamate (44). As described previously, treatment of compounds (44) with reagent (8) under various conditions as described in Scheme 1 affords compounds (45), which represent compounds of Formula I where E is O and J is C=O. Alternatively, compounds (43) can be treated with an aldehyde or ketone (46), with or without an acid catalyst, such as p-toluenesulfonic acid, and with or without heating, in a solvent such as ethanol or toluene, to afford compounds (47). As described previously, treatment of compounds (47) with reagent (8) under various conditions as described in Scheme 1 affords compounds (48), which represent compounds of Formula I where E is O and J is $CR_9R_9$.

Scheme 7

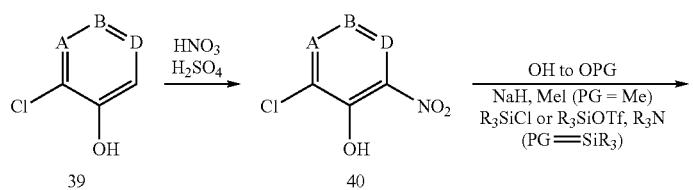

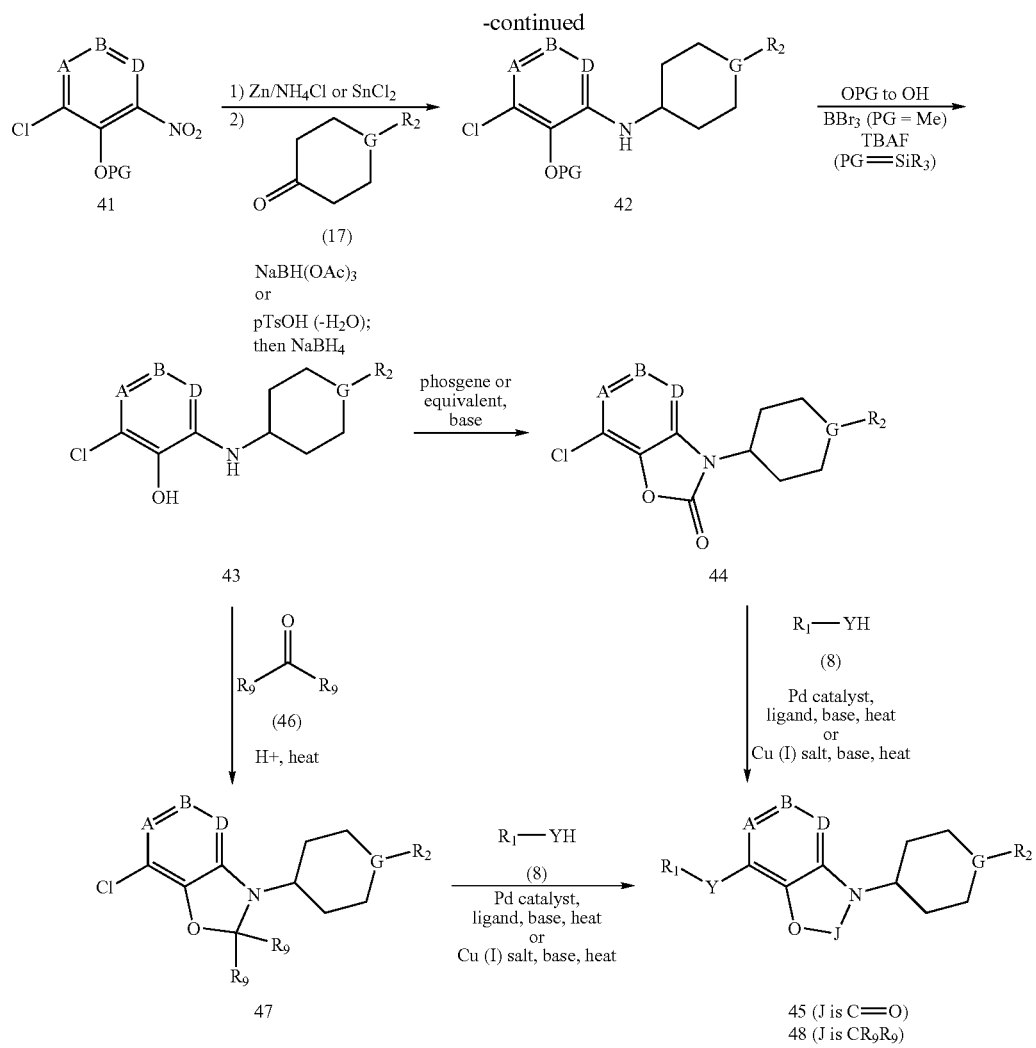

Alternatively, the compounds of formula I where E is O and J is C=O or CR$_9$R$_9$ can be prepared as described in Scheme 8. For certain compounds of formula (I), appropriate dichloro compounds such as (49), which are either commercially available or are readily prepared by standard procedures, can be used as starting material. Treatment of (49) with amine (2) in the presence of a base such as triethylamine or potassium carbonate, in a solvent such as THF or DMF, with or without heating, affords compounds (50). For example, treatment of commercially available 4,6-dichloro-5-methoxypyrimidine (49, A and D are N, B is CH) with 1 equivalent of amine (2) in the presence of potassium carbonate in DMF at room temperature affords (50, A and D are N, B is CH). Demethylation can be accomplished with BBr$_3$ or TMSI, as described in Scheme 7, to afford the hydroxyl compound (43). It will be recognized by those skilled in the art that when G is nitrogen and when R$_2$ is an acid labile protecting group, such as tert-butyloxycarbonyl (BOC), deprotection under acidic conditions may also cause loss of the nitrogen protecting group. In such case (G is N, R$_2$ is BOC) the nitrogen can be reprotected using di-tert-butyldicarbonate (BOC$_2$O) to afford (43). Treatment of (43) with phosgene in the presence of a base, or with an aldehyde or ketone (46), as described in Scheme 7, followed by coupling with an appropriate reagent (8), as described in Scheme 1, affords compounds (45) and (48), which represent compounds of Formula I where E is O and J is C=O or CR$_9$R$_9$, respectively.

Scheme 8

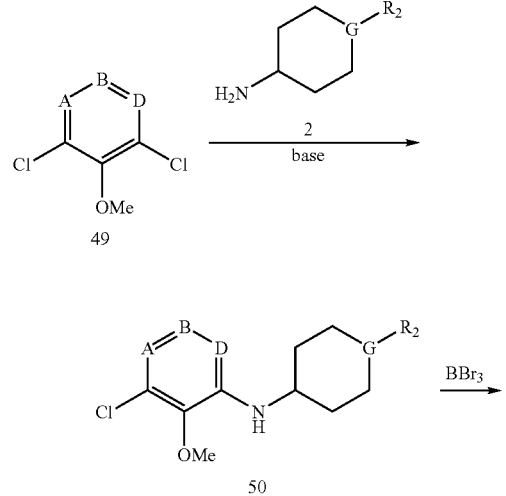

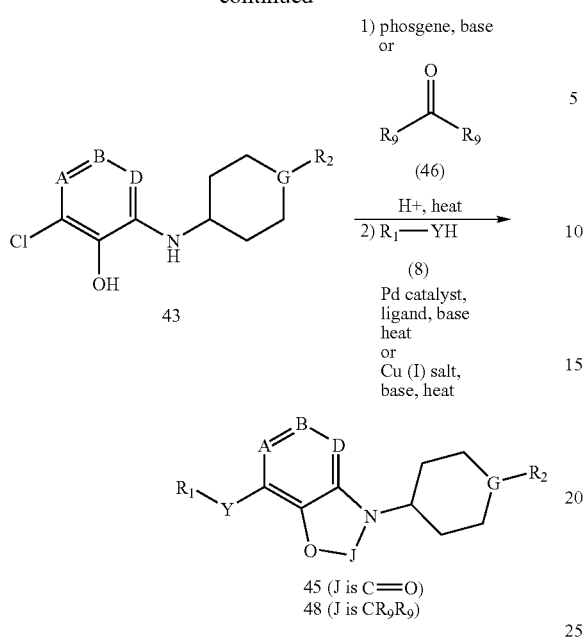

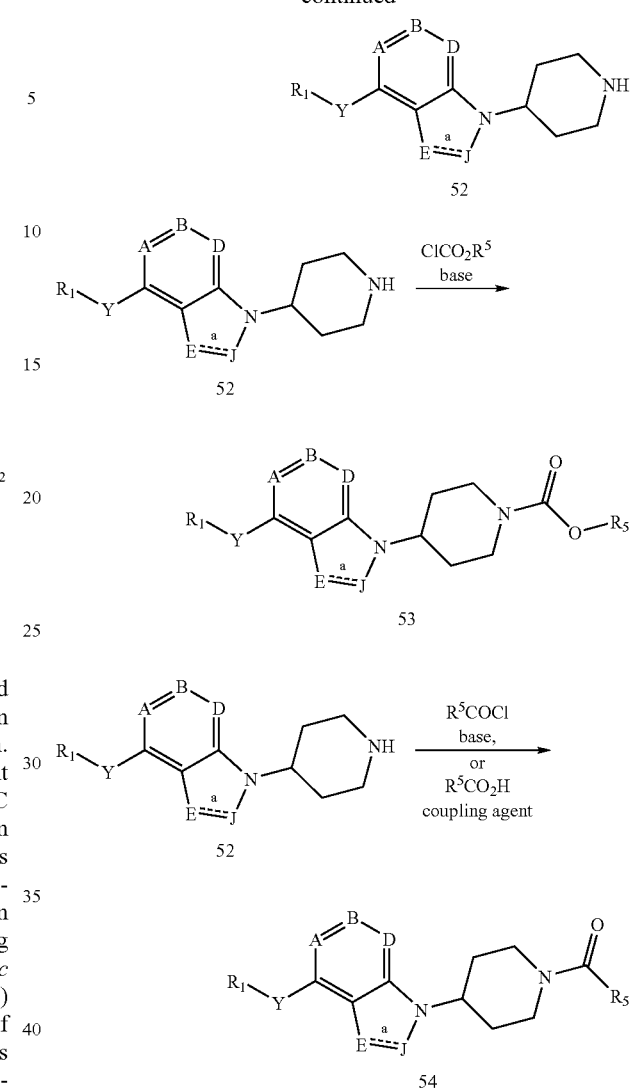

The nature of the R₂ group in Formula I can be varied readily by a variety of procedures known to those skilled in the art, for example as shown in Scheme 9 when G is nitrogen. When G is nitrogen, R₂ in the previous schemes can represent a nitrogen protecting group, such as but not limited to a BOC or CBZ carbamate. Deprotection of (51) when R₂ is BOC can be accomplished using HCl or TFA to give (52). When R₂ is CBZ, deprotection can be accomplished by catalytic hydrogenation to afford (52). It will be recognized to one skilled in the art that R₂ can take the form of a variety of protecting groups (see Greene, T. et al., *Protecting Groups in Organic Synthesis*, John Wiley & Sons, Inc., New York, N.Y. (1991) and references therein). Treatment of (52) with a variety of alkyl or aryl chloroformates, in the presence of a base such as triethylamine, in a solvent such as THF or methylene chloride, affords carbamates (53). Alternatively, treatment of (52) with acid chlorides in the presence of a base such as triethylamine, in a solvent such as THF or methylene chloride, or with carboxylic acids in the presence of a suitable peptide coupling agent, such as but not limited to 1-hydroxybenzotriazole (HOBT) or benzotriazol-1-yloxytris(pyrrolidino) phosphonium hexafluorophosphate (pyBOP), in a solvent such as THF or methylene chloride, affords the amides (54). One skilled in the art of organic synthesis will recognize that a wide variety of procedures are known for carrying out the transformation of (52) to (53) and (54).

Scheme 9

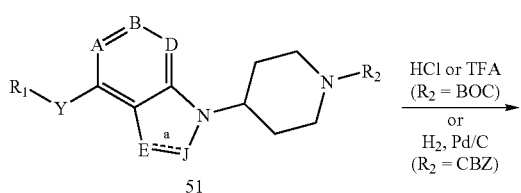

R2 = protecting group

Additional methods for varying the substituent R2 are described in Scheme 10, where G is nitrogen. Treatment of (52) with an optionally substituted aryl halide or aryl triflate (55) in the presence of a suitable palladium catalyst, ligand and base will afford the aryl substituted compounds (56) (see Yang, B. H. et al., *J. Organomet. Chem.*, 576:125 (1999) and references therein). Treatment of amine (52) with a cyclic ketone (57) in the presence of a reducing agent, such as sodium triacetoxyborohydride, affords cycloalkyl substituted analogs (59). Alternatively, treatment of (52) with a cyclic bromide or mesylate (58) in the presence of a base such as potassium carbonate or cesium carbonate in a solvent such as THF or DMF, with or without heating, provides the analogs (59). Amine (52) can also be treated with a variety of halogen-substituted 5 and 6-membered heterocyclic analogs (60) or (61), for example 2-chloropyrimidine, in the presence of a base such as potassium carbonate or sodium tert-butoxide in a solvent such as THF or DMF, with or without heating, or under a variety of palladium-catalyzed coupling conditions (see Yang, B. H. et al., *J. Organomet. Chem.*, 576:125 (1999) and references therein) to afford the heteroaryl substituted analogs (62).

41

Scheme 10

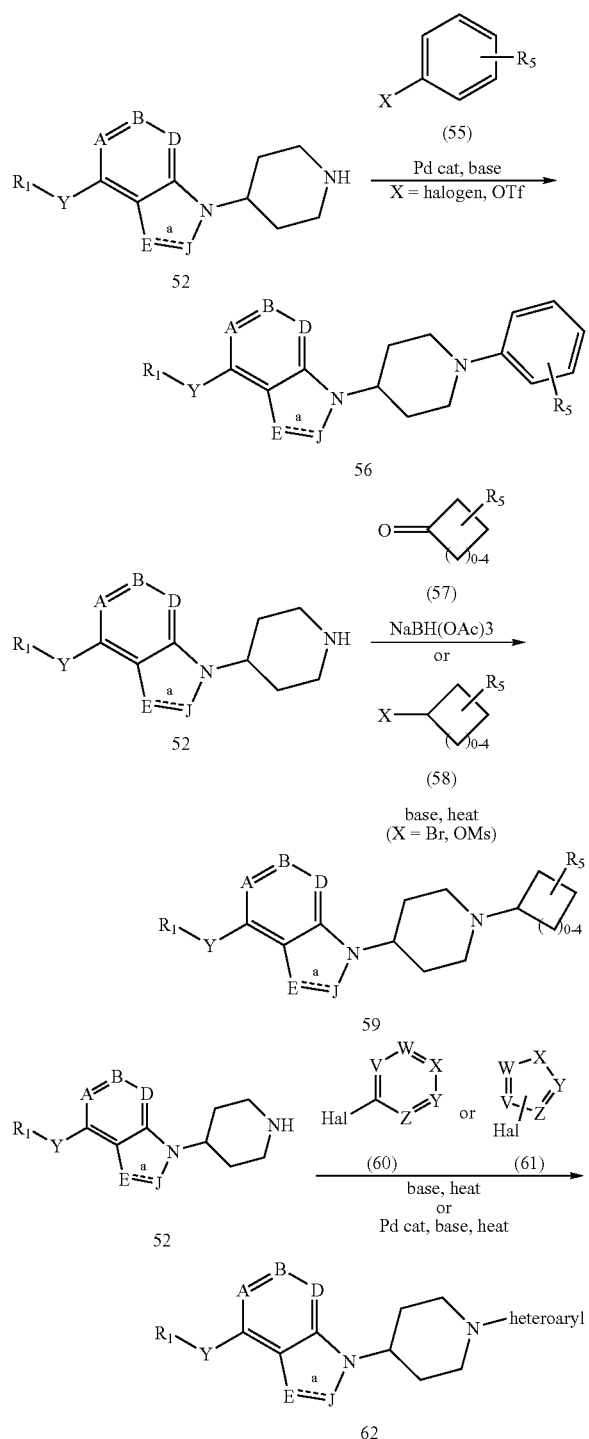

Utilities and Combinations

A. Utilities

The compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodistrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR119 receptor agonists or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl- N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar); SGLT2 inhibitors (e.g., 3-(Benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergliflozin (Kissei), AVE 2268 (Sanofi-Aventis)); 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, and denagliptin); glucagon-like peptide-1 (GLP-1) receptor agonists (e.g., Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™); aldose reductase inhibitors (e.g., those disclosed in WO 99/26659); RXR agonists (e.g., reglitizar (JTT-501), 5-[[6-[(2-fluorophenyl)methoxy]-2-naphthalenyl]methyl]-2,4-Thiazolidinedione (MCC-555), 5-[[3-(5,6,7,8-tetrahydro-3,5,5,8,8-pentamethyl-2-naphthalenyl)-4-(trifluoromethoxy)phenyl]methylene]-2,4-Thiazolidinedione (MX-6054), DRF2593, farglitazar, (±)-5-[(2,4-dioxothiazolidin-5-yl)methyl]-2-methoxy-N-[[(4-trifluoromethyl)phenyl]methyl]benzamide (KRP-297), 6-[1-(5,6,7,8-tetrahydro-3,5,5,8,8-pentamethyl-2-naphthalenyl) cyclopropyl]-3-Pyridinecarboxylic acid (LG100268)); fatty acid oxidation inhibitors (e.g., clomoxir, etomoxir; α-glucosidase inhibitors: precose, acarbose, miglitol, erniglitate, voglibose, 2,6-dideoxy-2,6-imino-7-O-β-D-glucopyranosyl-D-glycero-L-gulo-heptitol (MDL-25,637), camiglibose); beta-agonists (e.g., Methyl ester [4-[(2R)-2-[[(2R)-2-(3-chlorophenyl)-2-hydroxyethyl]amino]propyl]phenoxy]-Acetic acid (BRL 35135), 2-[4-[(2S)-2-[[(2S)-2-(3-chlorophenyl)-2-hydroxyethyl]amino]propyl]phenoxy]-Acetic acid (BRL 37344), 4-[(3R)-3-[bis[(2R)-2-hydroxy-2-phenylethyl]amino]butyl]-Benzamide (Ro 16-8714), 2-[4-[2-[[(2S)-2-hydroxy-3-phenoxypropyl]amino]ethoxy]phenoxy]-N-(2-methoxyethyl)-Acetamide (ICI D7114), 5-[(2R)-2-[[(2R)-2-(3-chlorophenyl)-2-hydroxyethyl] amino]propyl]-3-Benzodioxole-2,2-dicarboxylic acid, disodium salt (CL 316,243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386, 398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-Cyclohexadiene-1,4-dione (L-783281), TER17411, TER17529); gluconeogenesis inhibitors (e.g., GP3034); somatostatin analogs and antagonists; antilipolytic agents (e.g., nicotinic acid, acipimox, N-cyclohexyl-2'-O-methyl-Adenosine (WAG 994)); glucose transport stimulating agents (e.g., 4-chloro-α-[(4-methylphenylsulfolyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (Karo Bio)); Glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-Pyridinecarboxylic acid (GKA-50 AstraZeneca)); GPR119 agonists (e.g., 1,1-dimethylethyl ester 4-[[3-(4-pyridinyl)-1,2,4-oxadiazol-5-yl]methoxy]-1-Piperidinecarboxylic acid (PSN-632408 OSI Prosidion)); GDIR agonists (e.g., APD668 (Arena)); GPR40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy)phenyl)-1H-benzo[d]imidazole).

Examples of suitable lipid lowering agents and anti-atherosclerotic agents for use in combination with the compounds of the present invention include one or more MTP/ApoB secretion inhibitors (e.g., dirlopatide, N-(2,2,2-Trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid cotransporter inhibitors (e.g., compounds as disclosed in Drugs of the Future, 24, 425-430 (1999); upregulators of LDL receptor activity (e.g., (3R)-3-[(13R)-13-hydroxy-10-oxotetradecyl]-5,7-dimethoxy-1(3H)-Isobenzofuranone (Taisho Pharmaceutical Co. Ltd) and (3α,4α,5α)-4-(2-propenyl)-Cholestan-3-ol (Eli Lilly); bile acid sequestrants (e.g., WELCHOL®, COLESTID®, LOCHOLEST® AND QUESTPAN®; and fibric acid derivatives, such as ATROMID®, LOPID® AND TRICOT®); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolyties (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl) sulfonyl]-4,5-dihydro-N'-methyl-4-phenyl-1H-Pyrazole-1-carboximidamide (SLV 319), CP-945598 (Pfizer), Surinabant (SR-147778, Sanofi-Aventis), N-[(1S,2S)-3-(4-Chlorophenyl)-2-(3-cyanophenyl)-1-methylpropyl]-2-methyl-2-{[5-(trifluoromethyl)pyridin-2-yl] oxy}propanamide (Merck) and those discussed in Hertzog, D. L., *Expert Opin. Ther. Patents*, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-Benzenesulfonamide (L750355, Merck), or CP331648 (Pfizer) or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-Benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buprogrion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b][1,4]diazepino[6,7,1hi]indole]: with lorcaserin hydrochloride being preferred); 5-HT6 receptor antagonists (SUVEN, BIOVITRUM, EPIX), anti-epileptics topiramate (Johnson & Johnson) and zonisamide, a ciliary neurotrophic factor agonist (eg. axokine (REGENERON); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer)); acetyl-CoA carboxylase (ACC) inhibitors (e.g., N-(4-(4-(4-isopropoxyphenoxy)phenyl)but-3-yn-2-yleacetamide (A-80040, Abbott), (R)-anthracen-9-yl(3-(morpholine-4-carbonyl)-1,4'-bipiperidin-1'-yl)methanone (CP-640186, Pfizer)), SCD-1 inhibitors as described by Jiang et al, Diabetes 2004, 53, (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH2 (Unigene)), NPY-Y4 agonists (7™ Pharma WO 2005/089786(A2,A3)-1), NPY-5 antagonists (e.g., NPY5RA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-2789513); galanin receptor antagonists; MCR-4 antagonists (e.g., N-acetyl-L-norleucyl-L-glutaminyl-L-histidyl-D-phenylalanyl-L-arginyl-D-tryptophyl-Glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to ARICEPT®, RAZADYNE®, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

Assay(s) for GPR119 G Protein-Coupled Receptor Activity

The in vitro modulation of GPR119 was determined as follows.
HIT-T15 cAMP Assay

A HIT-T15 hamster insulinoma cell line was purchased from ATCC and grown in the medium recommended by ATCC (i.e., Growth Medium: F12K Medium (Invitrogen 21127-022; 10% D-horse Serum; and 2.5% FBS).

To conduct the cAMP assay, cells are plated on 96 well plates (e.g., BD Falcon; REF 353948, black side, clear bottom, TC surface) at a density of about $4.5 \times 10^4$ cells per well in growth medium and incubated overnight. Following incubation, the growth medium is removed from the wells followed by a single rinse with the assay buffer from the Hit Hunter cAMP kit (100 µl/well). Following the rinse, 20 µl of assay buffer is added to each well followed by addition of 10 µl of a 3× concentration of compound working solution. The solution is then mixed well. The final concentration range of compound is from about $10^{-5}$ M to about $10^{-11}$ M. The reaction is incubated at 37° C., in a 5% $CO_2$ for 1 hour. Following incubation, the cAMP concentration is determined using the Hit Hunter cAMP kit according to the manufacturer's protocol.
Human Tet-Inducible cAMP Assay Cell lines using the Flp-In-T-REx 293 tetracycline inducible gene expression system are cultured in culture medium comprising the following components: DMEM#11965, 100% FBS, 2 mM L-glutamine, 200 ug/ml Hygromycin B, and 15 ug/ml blasticidin.

For cAMP assays, cells are plated on 96 well plates (e.g., BD Falcon: REF 353948, black side, clear bottom, TC surface) at a density of about $4.5 \times 10^4$ cells per well in growth medium containing 1.0 ug/ml tetracycline (1.0 mg/ml stock). The cells are then incubated for 48 hours at 37° C.

Following the incubation, the growth medium is removed from the wells and the wells rinsed (once) with the assay buffer included in the Hit Hunter cAMP kit (100 µl/well). Following the wash, 20 µl of assay buffer is added to each well, followed by addition of 10 µl of a 3× concentration compound working solution. The solution is then mixed. The final concentration range of compound is from about $10^{-5}$ M to about $10^{-11}$ M. The reagents are then incubated at 37° C. at 5% $CO_2$ for 1 hour.

The manufacturer's protocol may be followed for cAMP determination. The Hit Hunter cAMP kit protocol is outlined for the HIT-T15 cAMP assays described above.
Luciferase Assay HEK 293 cells may be plated on poly-D-lysine treated 96-well BD black side/clear bottom plates at a density of about $3 \times 10^4$ cells/well in growth medium. The growth medium may comprise the following: D-MEM (Cat #12430) with high glucose and 10% fetal bovine serum.

Cells may be transfected with vectors comprising native or non-native GPR119 sequences using commercially available vectors (e.g., Stratagene) and transfection reagents. The standard manufacturer's protocols may be followed to transfect the cells. Following transfection, the transfection medium may be removed and assay medium added to the wells of the assay plates.

Once the assay plates are prepared, compound dilution plates may be made. To do so, make a first compound dilution plate using 10 mM of the compound of interest diluted to about 1 mM in DMSO. Then make 12 point half-log dilutions of the compounds (in DMSO) using an automated liquid handler. Next, make a second dilution plate by diluting the wells in the first plate ten fold (10×) using assay medium. Once the plates are complete, the highest dose is about 10 µM and the lowest dose is about 0.03 nM.

Once the dilution plates are complete, one can add about 10 µl of the 10× compound dilution to the assay plate containing the assay medium transiently transfected cells. Tap the plate to mix the reagents and incubate the plate overnight at 37° C., 95% $O_2$, and 5% $CO_2$ in an incubator.

Following incubation, a luciferase assay system may be used (e.g., Stead-Glo Luciferase Assay System from Promega) according to the manufacturer's instructions. Following completion of the reaction, immediately measure the readout of the assay using a top count luminometer.

In general, preferred compounds of the present invention, such as particular compounds disclosed in the following examples, have been identified to modulate the functional activity of GPR119 G protein-coupled receptor at concentrations equivalent to, or more potently than, 10 µM, preferably 5 M, more preferably 1 µM, and still more preferably 0.1 µM, thereby demonstrating compounds of the present invention as especially effective modulators of GPR119 G protein-coupled receptor. Potencies can be calculated and expressed as $EC_{50}$ values, and refer to activity measured employing the assay system described above.

Abbreviations

The following abbreviations are employed in the Examples and elsewhere herein:

| | |
|---|---|
| EtOAc = | ethyl acetate |
| DMF = | dimethylformamide |
| THF = | tetrahydrofuran |
| $K_2CO_3$ = | potassiumm carbonate |
| $Na_2CO_3$ = | sodium carbonate |
| $MgSO_4$ = | magnesium sulfate |
| $SiO_2$ = | Silicon Dioxide |
| $CH_2Cl_2$ = | methylene chloride |
| MeOH = | methanol |
| HCl = | hydrochloric acid |
| $Cs_2CO_3$ = | cesium carbonate |
| KOH = | potassium hydroxide |
| DME = | 1,2-dimethoxyethane |
| $Pd(dppf)Cl_2$ = | [1,1'-bis(diphenylphosphino)ferrocene] dichloropalladium (II) |
| t-BuONa = | sodium tert-butoxide |
| $Pd_2(dba)_3$ = | tris(dibenzylideneacetone)dipalladium (0) |
| BINAP = | rac-2,2'-bis(diphenylphosphino)-1,1'-binaphthyl |
| $NaHCO_3$ = | sodium bicarbonate |
| $SnCl_2 \cdot 2H_2O$ = | stannous chloride |
| $NaNO_2$ = | sodium nitrite |
| min = | minute(s) |
| h or hr = | hour(s) |
| mL or ml = | milliliter |
| g = | gram(s) |
| mg = | milligram(s) |
| mmol = | millimole(s) |
| µM = | micormolar |
| nM = | nanomolar |
| LRMS = | low resolution mass spectrometry |

| | |
|---|---|
| NMR = | nuclear magnetic resonance |
| sat or sat'd = | saturated |
| aq. = | aqueous |

EXAMPLES

The following working Examples serve to better illustrate, but not limit, some of the preferred embodiments of the present invention. Unless otherwise indicated, they have been prepared, isolated and characterized using the methods disclosed herein. The abbreviations and terms used herein are defined above. Chemical symbols have their usual and customary meanings.

Example 1 tert-Butyl 4-(4-(2-fluoro-4-(methylsulfonyl)phenylamino)-1H-[1,2,3]triazolo[4,5-c]pyridin-1-yl)piperidine-1-carboxylate

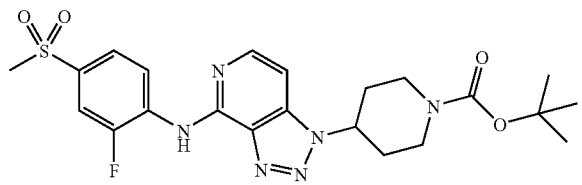

Example 1A tert-Butyl 4-(2-chloro-3-nitropyridin-4-ylamino)piperidine-1-carboxylate

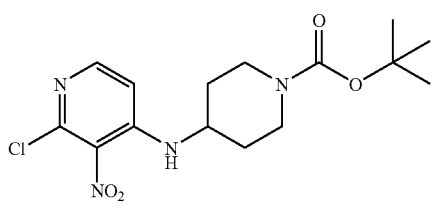

To a solution of 2,4-dichloro-3-nitropyridine (0.60 g, 3.1 mmol) in 10 mL of N,N-dimethylformamide was added potassium carbonate (0.64 g, 4.65 mmol) and tert-butyl 4-aminopiperidine-1-carboxylate (0.62 g, 3.1 mmol). Upon completion of addition, the reaction mixture was stirred at ambient temperature for 3 h. After this time, the reaction mixture was diluted with ethyl acetate, washed with 1N HCl and brine, dried over MgSO$_4$ and then concentrated to a yellow oil. The yellow oil was purified by flash chromatography on silica gel (elution with 1:1 EtOAc/hexane) to afford 0.65 g (59%) of Example 1A as a yellow solid. $^1$H NMR (CDCl$_3$): δ 8.01 (d, 1H, J=6.1 Hz), 6.64 (d, 1H, J=6.0 Hz), 6.48 (d, 1H, J=6.5 Hz), 4.08-3.98 (m, 2H), 3.60-3.52 (m, 1H), 3.00-2.90 (m, 2H), 2.05-1.95 (m, 2H), 1.50-1.42 (m, 2H), 1.44 (s, 9H). LRMS (ESI): 357.1/359.1 (M+H)+.

Example 1B tert-Butyl 4-(3-amino-2-chloropyridin-4-ylamino)piperidine-1-carboxylate

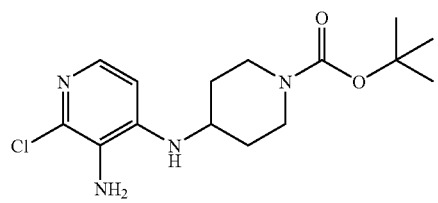

To a mixture of Example 1A (97 mg, 0.27 mmol) in 4 mL of methanol was added ammonium chloride (73 mg, 1.4 mmol) and zinc dust (353 mg of <10μ, 5.4 mmol). There was a slight exotherm, and the resulting suspension was stirred at ambient temperature for 1 h. At the conclusion of this period, the reaction mixture was diluted with EtOAc to about 5:1 EtOAc/methanol. The resulting mixture was filtered through a pad of silica gel/CELITE® 545 filter aid and then concentrated to afford 85 mg (96%) of Example 1B as a pale solid, which was without further purification. $^1$H NMR (CDCl$_3$): δ 7.71 (d, 1H, J=4.9 Hz), 6.43 (d, 1H, J=5.5 Hz), 4.24 (broad s, 1H), 4.12-4.02 (m, 2H), 3.49 (broad s, 2H), 3.46-3.40 (m, 1H), 2.95-2.87 (m, 2H), 2.05-1.98 (m, 2H), 1.45 (s, 9H), 1.44-1.35 (m, 2H). LRMS (ESI): 327.1/329.0 (M+H)+.

Example 1C tert-Butyl 4-(4-chloro-1H-[1,2,3]triazolo[4,5-c]pyridin-1-yl)piperidine-1-carboxylate

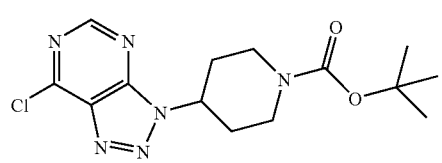

To a solution of Example 1B (43 mg, 0.13 mmol) in 1 mL of glacial acetic acid was added sodium nitrite (14 mg, 0.20 mmol) in 0.2 mL of water. Upon completion of addition, the reaction mixture was stirred at ambient temperature for 1 h. After this time, the reaction mixture was diluted with ethyl acetate, washed with sat'd aq NaHCO$_3$ and brine, dried over MgSO$_4$, filtered through a pad of silica gel, and then concentrated to afford 43 mg (98%) of Example 1C as a solid. $^1$H NMR (CDCl$_3$): δ 8.25 (d, 1H, J=5.5 Hz), 7.38 (d, 1H, J=5.5 Hz), 4.82-4.77 (m, 1H), 4.35-4.25 (m, 2H), 3.00-2.90 (m, 2H), 2.30-2.20 (m, 2H), 2.15-2.08 (m, 2H), 1.43 (s, 9H). LRMS (ESI): 338.1 (M+H)+.

Example 1

To a solution of Example 1C (40 mg, 0.12 mmol) in 2 mL of degassed toluene was added 2-fluoro-4-(methylsulfonyl)aniline (23 mg, 0.12 mmol), (±)-BINAP (4 mg, 0.006 mmol), t-BuONa (12 mg, 0.12 mmol) and Pd(dppf)Cl$_2$, (complex with CH$_2$Cl$_2$, 3 mg, 0.004 mmol). Upon completion of addition, the reaction mixture was stirred in a sealed vial at 110° C. for 4 h. After this time, the reaction mixture was cooled, diluted with ethyl acetate, washed with 1N HCl, sat'd aq NaHCO$_3$ and brine, dried over MgSO$_4$, and then concentrated to yield a residue. The residue was purified by flash chromatography on silica gel (elution with 1:1 hexane/ethyl acetate) to yield a solid. The solid was triturated with 1:1 ethyl acetate/ether and then with ether and then dried in vacuo to afford 15 mg (26%) of Example 1 as a white solid. $^1$H NMR (DMSO-D$_6$): δ 9.80 (broad s, 1H), 8.22 (dd, 1H), 8.03 (d, 1H, J=6.1 Hz), 7.82 (dd, 1H, J=8.8, 2.2 Hz), 7.75 (d, 1H, J=8.8 Hz), 7.37 (d, 1H, J=6.0 Hz), 5.10-5.02 (m, 1H), 4.15-4.07 (m, 2H), 3.26 (s, 3H), 3.08-2.98 (m, 2H), 2.17-2.11 (m, 2H), 2.07-1.98 (m, 2H), 1.43 (s, 9H). LRMS (ESI): 491.0 (M+H)+.

Example 2 tert-Butyl 4-(4-(4-(methylsulfonyl)phenoxy)-1H-[1,2,3]triazolo[4,5-c]pyridin-1-yl)piperidine-1-carboxylate

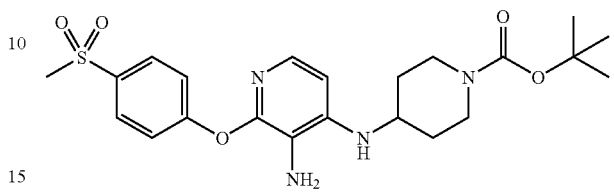

Example 2A tert-Butyl 4-(2-(4-(methylsulfonyl)phenoxy)-3-nitropyridin-4-ylamino)piperidine-1-carboxylate

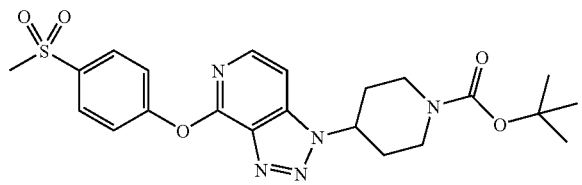

To a solution of Example 1A (265 mg, 0.74 mmol) in 5 mL of DMF was added potassium carbonate (0.15 g, 1.11 mmol) and 4-(methylsulfonyl)phenol (0.13 g, 0.74 mmol). Upon completion of addition, the reaction mixture was stirred at 60° C. for 18 h. At the conclusion of this period, the reaction mixture was cooled, diluted with ethyl acetate, washed with 1N HCl and brine, dried over MgSO$_4$ and then concentrated to yield a yellow solid. The yield solid was stirred in warm 2:1 hexane/ethyl acetate, cooled and then filtered to yield a solid. The solid was dried in vacuo to afford 0.27 g (75%) of Example 2A as a light yellow solid. $^1$H NMR (CDCl$_3$): δ 7.95 (d, 2H, J=8.8 Hz), 7.80 (d, 11, J=6.6 Hz), 7.38 (d, 2H, J=8.8 Hz), 7.27 (d, 1H, J=8.2 Hz), 6.90 (d, 1H, J=6.6 Hz), 3.95-3.88 (m, 2H), 3.80-3.73 (m, 1H), 3.23 (s, 3H), 2.92-2.82 (m, 2H), 1.86-1.80 (m, 2H), 1.50-1.42 (m, 2H), 1.40 (s, 9H). LRMS (ESI): 493.0 (M+H)+.

Example 2B tert-Butyl 4-(3-amino-2-(4-(methylsulfonyl)phenoxy)pyridin-4-ylamino)piperidine-1-carboxylate

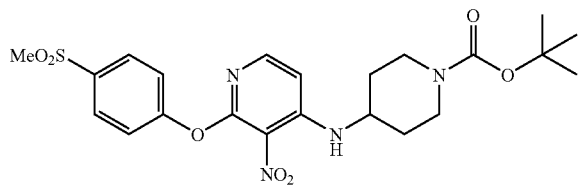

To a mixture of Example 2A (237 mg, 0.48 mmol) in 12 mL of methanol was added ammonium chloride (128 mg, 2.4 mmol) and zinc dust (630 mg of <10μ, 9.6 mmol). There was a slight exotherm, and the resulting suspension was stirred at ambient temperature for 2 h. The resulting mixture was diluted with EtOAc to about 5:1 EtOAc/methanol, filtered through a pad of silica gel/CELITE® 545 filter aid and then concentrated to yield a solid. This material was triturated with warm 3:1 hexane/EtOAc, filtered, washed with ether and dried in vacuo to afford 160 mg (73%) of Example 2B as a pale solid. $^1$H NMR (CDCl$_3$); δ 7.86 (d, 2H, J=8.8 Hz), 7.30 (d, 1H, J=5.5 Hz), 7.14 (d, 2H, J=8.8 Hz), 6.47 (d, 1H, J=5.5 Hz), 5.43 (d, 1H, J=7.2 Hz), 4.56 (broad s, 2H), 3.98-3.88 (m, 2H), 3.58-3.52 (m, 1H), 3.17 (s, 3H), 2.96-2.84 (broad m, 2H), 1.95-1.88 (m, 2H), 1.40 (s, 9H), 1.35-1.25 (m, 2H). LRMS (ESI): 463.1 (M+H)+.

Example 2

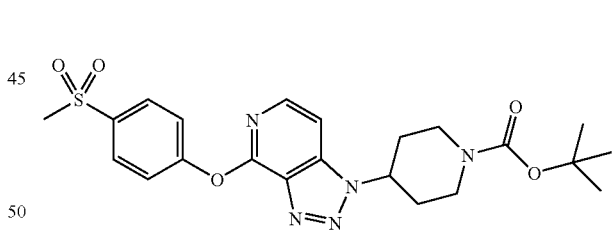

To a solution of Example 2B (25 mg, 0.05 mmol) in 0.5 mL of glacial acetic acid was added sodium nitrite (6 mg, 0.08 mmol) in 0.1 mL of water. Upon completion of addition, the reaction mixture was stirred at ambient temperature for 1 h. After this time, the reaction mixture was diluted with ethyl acetate, washed with sat'd aq NaHCO$_3$ and brine, dried over MgSO$_4$, filtered through a pad of silica gel, and then concentrated to yield a solid. The solid was triturated twice with ether and concentrated in vacuo to afford 16 mg (64%) of Example 2 as an off-white solid. $^1$H NMR (DMSO-D$_6$): δ 8.02 (d, 2H, J=8.8 Hz), 8.01 (d, 1H, J=6.0 Hz), 7.74 (d, 1H, J=6.0 Hz), 7.58 (d, 2H, J=8.8 Hz), 5.18-5.11 (m, 1H), 4.15-4.07 (m, 2H), 3.28 (s, 3H), 3.10-3.00 (m, 2H), 2.18-2.12 (m, 2H), 2.08-2.01 (m, 2H), 1.43 (s, 9H). LRMS (ESI): 474.1 (M+H)+.

Example 3 tert-Butyl 4-(7-(2-fluoro-4-(methylsulfonyl)phenylamino)-3H-[1,2,3]triazolo[4,5-d]pyrimidin-3-yl)piperidine-1-carboxylate

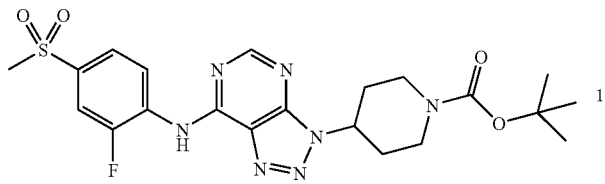

Example 3A tert-Butyl 4-(6-chloro-5-nitropyrimidin-4-ylamino)piperidine-1-carboxylate

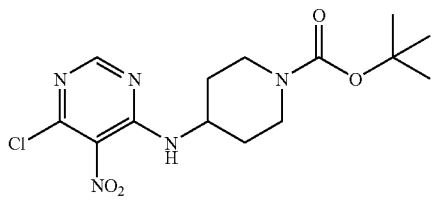

To a mixture of 4,6-dichloro-5-nitropyrimidine (3.88 g, 20 mmol) and 4-amino-1-BOC-piperidine (4.0 g, 20 mmol) in DMF (250 mL) was added K$_2$CO$_3$ (2.76 g, 20 mmol). Upon completion of addition, the reaction mixture was allowed to stir at ambient temperature for about 16 h. After this time, the reaction mixture was diluted with ethyl acetate, washed with water and brine, dried over MgSO$_4$ and concentrated to yield a residue. The residue was purified by flash chromatography on silica gel (elution with 0-50% EtOAc/hexane) to afford 4.01 g (58%) of Example 3A as a green-yellow solid. $^1$H NMR (400 MHz, CDCl$_3$): δ 1.48 (s, 9H), 1.50 (m, 2H), 2.05 (dd, 2H, J=2.7, 7.7 Hz), 2.95 (broad s, 2H), 4.10 (m, 2H), 4.32 (m, 1H), 7.40 (d, 1H, J=7.1 Hz), 8.38 (d, 1H, J=7.1 Hz). LRMS (ESI): 358.1 [M+H]$^+$.

Example 3B tert-Butyl 4-(5-amino-6-chloropyrimidin-4-ylamino)piperidine-1-carboxylate

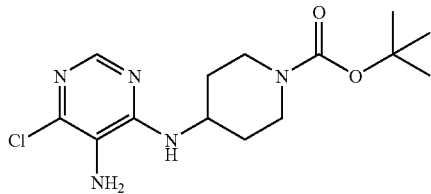

To a solution of Example 3A (1.85 g, 5.2 mmol) in THF (100 mL), SnCl$_2$.2H$_2$O (2.44 g, 10.8 mmol) was added portion-wise. Upon completion of addition, the reaction mixture was allowed to stir at ambient temperature for about 16 h. After this time, the reaction mixture was filtered and then concentrated to yield a residue. The residue was purified by flash chromatography on silica gel (elution with 0-10% MeOH/DCM) to afford 1.02 g (60%) of Example 3B as a yellow solid. LRMS (ESI): 328.1 [M+H]$^+$.

Example 3C tert-Butyl 4-(7-chloro-3H-[1,2,3]triazolo[4,5-d]pyrimidin-3-yl)piperidine-1-carboxylate

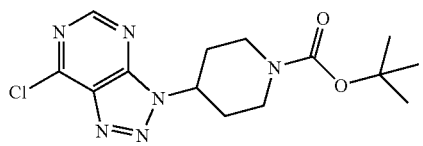

To a solution of Example 3B (328 mg, 1.0 mmol) in 5 mL of acetic acid was added NaNO$_2$ (104 mg, 1.5 mmol, in 0.5 mL of water) dropwise. Upon completion of addition, the reaction mixture was allowed to stir at ambient temperature for 30 min. At the conclusion of this period, the reaction mixture was filtered and concentrated to yield a residue. The residue was purified by flash chromatography on silica gel (elution with 0-100% EtOAc/Hex) to afford 119 mg (60%) of Example 3C as a pale solid. LRMS (ESI): 339.1 [M+H]$^+$.

Example 3 tert-Butyl 4-(7-(2-fluoro-4-(methylsulfonyl)phenylamino)-3H-[1,2,3]triazolo[4,5-d]pyrimidin-3-yl)piperidine-1-carboxylate Example 3 was prepared from Example 3C using a similar method as described above for Example 1. The crude residue was purified by flash chromatography on silica gel (0-75% hexane/EtOAc eluent) to afford Example 3 as a solid. $^1$H NMR (400 MHz, CDCl$_3$): δ 1.51 (s, 9H), 2.10 (m, 2H), 2.41 (m, 2H), 3.03 (m, 2H), 3.10 (s, 3H), 4.34 (broad s, 2H), 5.01 (m, 1H), 7.80 (m, 2H), 8.37 (s, 1H), 8.72 (s, 1H), 8.15 (d, 1H). LRMS (ESI): 436.0 [M+H—C$_4$H$_8$]$^+$.

Example 4 tert-Butyl 4-(6-(4-cyano-2-fluorophenylamino)-9H-purin-9-yl)piperidine-1-carboxylate

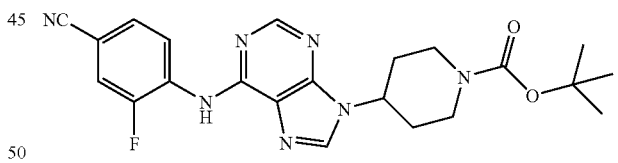

Example 4A tert-Butyl 4-(6-chloro-9H-purin-9-yl)piperidine-1-carboxylate

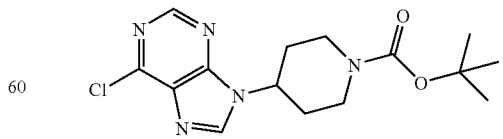

A mixture of Example 3B (480 mg, 1.46 mmol) and 10 mg of p-toluenesulfonic acid in 5 mL of triethyl orthoformate was allowed to stir at 110° C. for about 16 h. At the conclusion of this period, the reaction was purified by flash chromatography on silica gel (elution with 0-100% EtOAc/Hex) to afford 381 mg (77%) of Example 4A as a white solid. $^1$H NMR (400 MHz, CDCl$_3$): δ 1.50 (s, 9H), 2.05-2.22 (m, 4H), 2.96 (broad s, 2H), 4.38 (broad s, 2H), 4.71 (m, 1H), 8.19 (s, 1H), 8.75 (d, 1H, J=6.0 Hz). LRMS (ESI): 338.1 [M+H]$^+$.

Example 4 tert-Butyl 4-(6-(4-cyano-2-fluorophenylamino)-9H-purin-9-yl)piperidine-1-carboxylate Example 4 was prepared from Example 4A using a similar method as described above for Example 1. The crude residue was purified by flash chromatography on silica gel (0-75% hexane/EtOAc eluent) to afford Example 4 as a solid. $^1$H NMR (400 MHz, CDCl$_3$): δ 1.51 (s, 9H), 2.05 (m, 2H), 2.21 (m, 2H), 2.96 (broad s, 2H), 4.37 (broad s, 2H), 4.67 (m, 1H), 7.44 (dd, 1H, J=2.2, 11.0 Hz), 7.52 (d, H, J=8.8 Hz), 7.96 (d, 1H, J=9.9 Hz), 8.04 (d, 1H, J=2.7 Hz), 8.62 (s, 1H), 7.44 (dd, 1H, J=8.0, 8.5 Hz). LRMS (ESI); 438.1 [M+H]$^+$.

Example 5 tert-Butyl 4-(4-(2-chloro-4-cyanophenylamino)-1H-[1,2,3]triazolo[4,5-c]pyridin-1-yl)piperidine-1-carboxylate

To a solution of Example 1C (143 mg, 0.42 mmol) in 8 mL of degassed toluene was added 4-amino-3-chlorobenzonitrile (64 mg, 0.42 mmol), (±)-BINAP (13 mg, 0.02 mmol), sodium tert-butoxide (40 mg, 0.42 mmol) and Pd(dppf)Cl$_2$ (complex with CH$_2$Cl$_2$, 9 mg, 0.013 mmol). Upon completion of addition, the reaction mixture was heated under microwave irradiation at 110° C. for 1 h. After this time, the reaction mixture was cooled, diluted with ethyl acetate, washed with brine, dried over MgSO$_4$, and concentrated to yield a residue. The residue was purified by flash chromatography on silica gel (elution with 1:1 hexane/ethyl acetate) to afford 100 mg (52%) of Example 5 as an off-white solid. $^1$H NMR (CDCl$_3$): δ 9.20 (d, 1H, J=8.8 Hz), 8.64 (broad s, 1H), 8.14 (d, 1H, J=6.0 Hz), 7.71 (d, 1H, J=1.7 Hz), 7.60 (dd, 1H, J=8.8, 1.6 Hz), 7.04 (d, 1H, J=6.0 Hz), 4.84-4.77 (m, 1H), 4.38-4.29 (m, 2H), 3.06-2.96 (m, 2H), 2.32-2.25 (m, 2H), 2.19-2.12 (m, 2H), 1.49 (s, 9H). LRMS (ESI): 454.1 (M+H)+.

Example 6 iso-Propyl 4-(7-(2-fluoro-4-(methylsulfonyl)phenylamino)-3H-[1,2,3]triazolo[4,5-d]pyrimidin-3-yl)piperidine-1-carboxylate

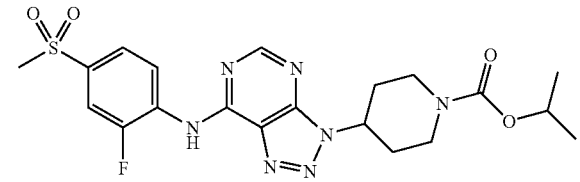

Example 6A

N-(2-fluoro-4-(methylsulfonyl)phenyl)-3-(piperidin-4-yl)-3H-[1,2,3]triazolo[4,5-d]pyrimidin-7-amine, HCl salt

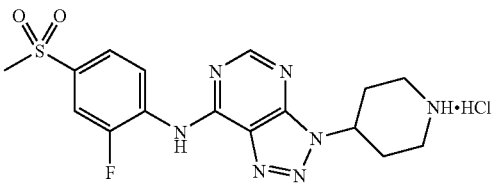

To Example 3 (97 mg, 0.197 mmol) in 1 ml of DCM was added 2 mL of 4M HCl in 1,4-Dioxane. The resulting solution was stirred at room temperature for 30 minutes, the reaction was evaporated in vacuum to yield 101 mg of crude Example 6A as a light yellow solid. LRMS (ESI); 392.2 [M+H]$^+$.

Example 6 iso-Propyl 4-(7-(2-fluoro-4-(methylsulfonyl)phenylamino)-3H-[1,2,3]triazolo[4,5-d]pyrimidin-3-yl)piperidine-1-carboxylate

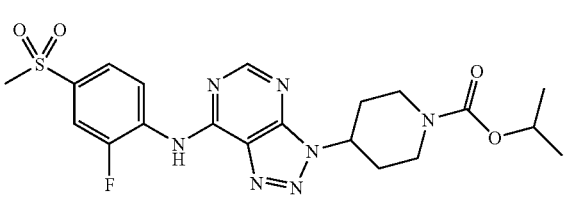

To Example 6A (70 mg, 0.179 mmol) and TEA (0.075 n, 0.537 mmol) in DCM (2 mL), isopropylchloroformate (1M in Toluene) (0.18 ml, 0.18 mmol) was added. The reaction was stirred at room temperature for 10 minutes. The reaction was evaporated in vacuo. The residue was purified by flash chromatography (eluted by 0-100% EtOAc/Hexane) to yield 7 mg (8%) of Example 6 as a pale solid. $^1$H NMR (500 MHz, CDCl$_3$): δ 1.22-1.32 (m, 6H) 2.18 (d, J=11.00 Hz, 2H) 2.34-2.48 (m, 2H) 2.98-3.12 (m, 5H) 4.38 (s, 2H) 4.90-5.08 (m, 2H) 7.75-7.81 (m, 1H) 7.83 (d, J=8.25 Hz, 1H) 8.44 (s, 1H) 8.71 (s, 1H) 9.07-9.16 (m, 1H). LRMS (ESI): 478.2 [M+H]$^+$.

Example 7 iso-Propyl 4-(7-(2-chloro-4-(methylsulfonyl)phenylamino)-3H-[1,2,3]triazolo[4,5-d]pyrimidin-3-yl)piperidine-1-carboxylate

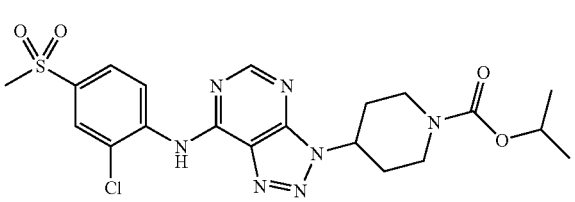

Example 7A tert-Butyl 4-(7-(2-chloro-4-(methylsulfonyl)phenylamino)-3H-[1,2,3]triazolo[4,5-d]pyrimidin-3-yl)piperidine-1-carboxylate

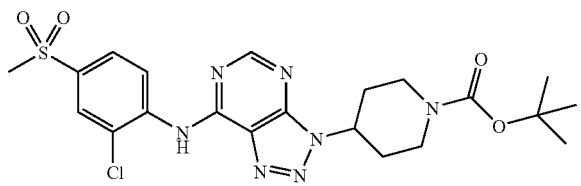

Example 7A was prepared from Example 3C using the same method described above for Example 1, with the exception that 2-fluoro-4-(methylsulfonyl)aniline was replaced with 2-chloro-4-(methylsulfonyl)aniline. LRMS (ESI): 508.1 [M+H]$^+$.

Example 7B

N-(2-Chloro-4-(methylsulfonyl)phenyl)-3-(piperidin-4-yl)-3H-[1,2,3]triazolo[4,5-d]pyrimidin-7-amine, HCl salt

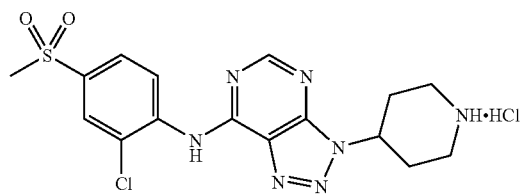

Example 7B was prepared from Example 7A using the same method described above for Example 6A. LRMS (ESI): 408.1 [M+H]$^+$.

Example 7 iso-Propyl 4-(7-(2-chloro-4-(methylsulfonyl)phenylamino)-3H-[1,2,3]triazolo[4,5-d]pyrimidin-3-yl)piperidine-1-carboxylate

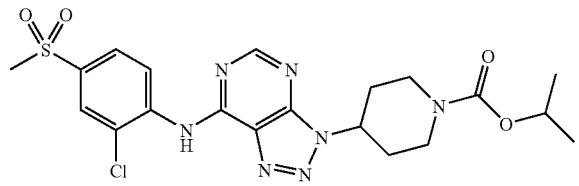

Example 7 was prepared from Example 7B using the same method described above for Example 6. $^1$H NMR (500 MHz, CDCl$_3$): δ 1.21-1.32 (m, 6H) 2.18 (d, J=11.55 Hz, 2H) 2.35-2.48 (m, 2H) 2.99-3.12 (m, 5H) 4.38 (s, 2H) 4.91-5.09 (m, 2H) 7.93 (dd, J=8.80, 2.20 Hz, 1H) 8.06 (d, J=2.20 Hz, 1H) 8.65-8.73 (m, 2H) 9.18 (d, J=8.80 Hz, 1H). LRMS (ESI): 494.1 [M+H]$^+$.

Example 8

N-(2-Fluoro-4-(methylsulfonyl)phenyl)-3-(1-(pyrimidin-2-yl)piperidin-4-yl)-3H-[1,2,3]triazolo[4,5-d]pyrimidin-7-amine

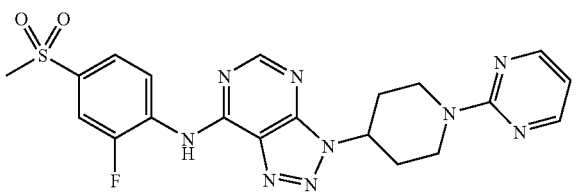

A mixture of Example 6A (30 mg, 0.070 mmol), 2-bromopyrimidine (11.15 mg, 0.070 mmol) and t-BuONa (13.48 mg, 0.140 mmol) in DMF (1 mL) was stirred at 100° C. overnight. The reaction was purified by flash chromatography (0-100% hexane/EtOAc eluent) to afford 12 mg (36.5%) of Example 8 as a solid. $^1$H NMR (500 MHz, CDCl$_3$): δ 2.72-2.83 (m, 2H) 3.00-3.13 (m, 5H) 4.78 (s, 2H) 4.95 (d, J=13.75 Hz, 2H) 5.14-5.24 (m, 1H) 6.58 (t, J=4.95 Hz, 1H) 7.78-7.88 (m, 2H) 7.99 (d, J=2.20 Hz, 1H) 8.32 (s, 1H) 8.42 (d, J=4.95 Hz, 2H) 8.99 (d, J=8.80 Hz, 1H). LRMS (ESI): 470.1 [M+H]$^+$.

Example 9

3-(1-(5-Ethylpyrimidin-2-yl)piperidin-4-yl)-N-(2-fluoro-4-(methylsulfonyl)phenyl)-3H-[1,2,3]triazolo[4,5-d]pyrimidin-7-amine

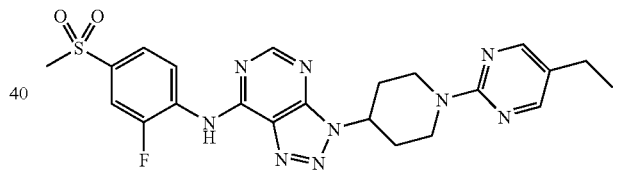

Example 9 was prepared from Example 6A using the same method described above for Example 8, with the exception that 2-bromopyrimidine was replaced with 2-chloro-5-ethylpyrimidine. $^1$H NMR (500 MHz, CDCl$_3$): δ 1.29 (t, J=7.70 Hz, 3H) 2.42 (dd, J=13.75, 3.30 Hz, 2H) 2.56 (q, J=0.45 Hz, 2H) 2.64 (q, J=7.70 Hz, 2H) 3.10 (s, 3H) 3.57 (t, J=11.55 Hz, 2H) 4.83 (d, J=14.30 Hz, 2H) 5.19-5.29 (m, 1H) 7.75-7.88 (m, 2H) 8.47 (s, 2H) 8.69 (s, 1H) 8.91 (s, 1H). LRMS (ESI): 498.3 [M+H]$^+$.

Example 10 iso-Propyl 4-(6-(2-fluoro-4-(methylsulfonyl)phenylamino)-9H-purin-9-yl)piperidine-1-carboxylate

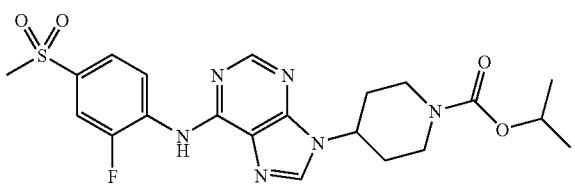

Example 10A tert-Butyl 4-(6-(2-fluoro-4-(methylsulfonyl)phenylamino)-9H-purin-9-yl)piperidine-1-carboxylate

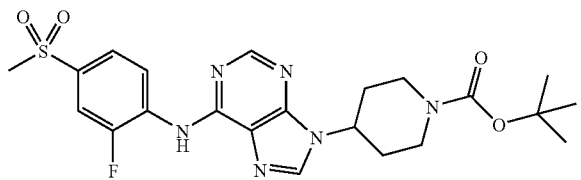

Example 10A was prepared from Example 4A using the same method described above for Example 1. LRMS (ESI): 491.2 [M+H]$^+$.

Example 10B

N-(2-Fluoro-4-(methylsulfonyl)phenyl)-9-(piperidin-4-yl)-9H-purin-6-amine, HCl salt

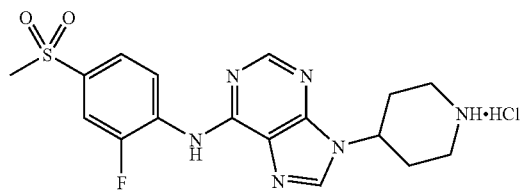

Example 10B was prepared form Example 10A using the same method described above for Example 6A. LRMS (ESI): 391.1 [M+H]$^+$.

Example 10 iso-Propyl 4-(6-(2-fluoro-4-(methylsulfonyl)phenylamino)-9H-purin-9-yl)piperidine-1-carboxylate

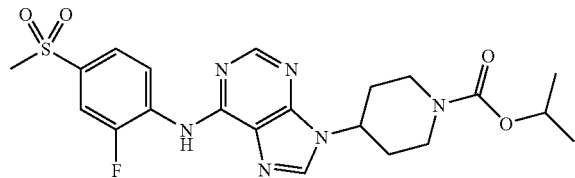

Example 10 was prepared from Example 10B using the same method described above for Example 6. $^1$H NMR (500 MHz, CDCl$_3$): δ 1.21-1.30 (m, 6H) 1.99-2.10 (m, 2H) 2.15-2.25 (m, 2H) 2.97 (s, 2H) 3.06 (s, 3H) 4.40 (s, 2H) 4.62-4.72 (m, 1H) 4.90-5.00 (m, 1H) 7.72 (dd, J=9.90, 2.20 Hz, 1H) 7.78 (d, J=8.80 Hz, 1H) 7.96 (s, 1H) 8.07 (d, J=3.30 Hz, 1H) 8.62 (s, 1H) 9.09-9.18 (m, 1H). LRMS (ESI): 477.1 [M+H]$^+$.

Example 11

N-(2-Fluoro-4-methylsulfonyl)phenyl)-9-(1-(pyrimidin-2-yl)piperidin-4-yl)-9H-purin-6-amine

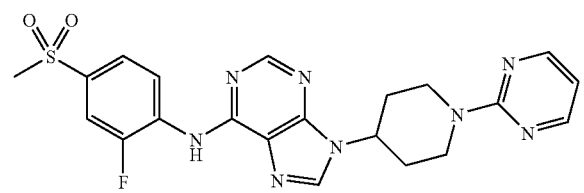

Example 11 was prepared from Example 10B using the same method described above for Example 8. $^1$H NMR (500 MHz, CDCl$_3$): δ 2.06-2.17 (m, 2H) 2.31 (d, J=12.10 Hz, 2H) 3.07 (s, 3H) 3.13 (t, J=12.92 Hz, 2H) 4.83 (t, J=12.10 Hz, 1H) 5.08 (d, J=13.75 Hz, 2H) 6.57 (s, 1H) 7.73 (d, J=10.45 Hz, 1H) 7.79 (d, J=8.80 Hz, 1H) 7.97 (s, 1H) 8.12 (s, 1H) 8.36 (d, J=4.40 Hz, 2H) 8.63 (s, 1H) 9.14 (t, J=7.97 Hz, 1H). LRMS (ESI): 469.2 [M+H]$^+$.

Example 12

Benzyl 4-(4-(2-fluoro-4-(methylsulfonyl)phenylamino)-1H-pyrazolo[3,4-d]pyrimidin-1-yl)piperidine-1-carboxylate

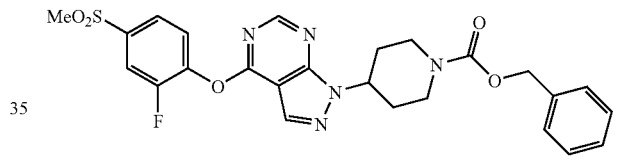

Example 12A

Benzyl 4-(2-(tert-butoxycarbonyl)hydrazinyl)piperidine-1-carboxylate

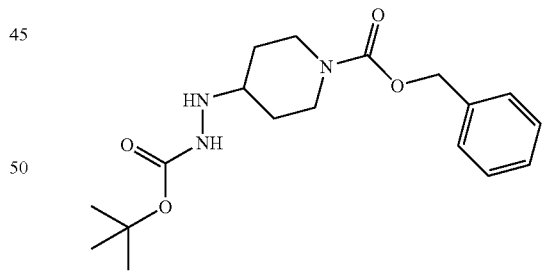

To a solution of benzyl 4-oxopiperidine-1-carboxylate (4.08 g, 17.5 mmol) in 50 mL of methanol was added tert-butylcarbazate (2.31 g, 17.5 mmol). The mixture was stirred at room temperature for 3 h and then was concentrated in vacuo to afford a white foam. This residue was taken up in 50 mL of 50% glacial acetic acid. To the resulting suspension was added sodium cyanoborohydride (1.1 g, 17.5 mmol) portionwise with vigorous stirring at room temperature. After the addition was complete the mixture was stirred for 3 h at room temperature. The mixture was neutralized with 1N NaOH/solid NaOH and then extracted twice with methylene chloride. The combined organics were washed with sat'd aq sodium bicarbonate and brine, dried (Na₂SO₄), filtered through a pad of silica gel and concentrated in vacuo to afford Example 12A, benzyl 4-(2-(tert-butoxycarbonyl)hydrazinyl)piperidine-1-carboxylate, as a solid (6.0 g) which was pure enough to be used without purification. LRMS (ESI): 350.1 (M+H)+.

Example 12B

Benzyl 4-(4-chloro-1H-pyrazolo[3,4-d]pyrimidin-1-yl)piperidine-1-carboxylate

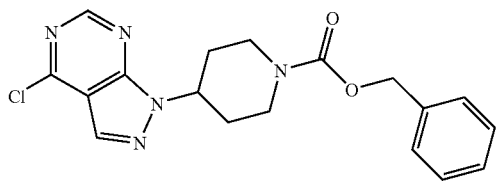

To a solution of 4,6-dichloropyrimidine-5-carbaldehyde (1.089 g, 6.15 mmol) and benzyl 4-(2-(tert-butoxycarbonyl)hydrazinyl)piperidine-1-carboxylate from Example 12A (2.15 g, 6.15 mmol) in dichloromethane (25 mL) was added triethylamine (2.144 mL, 15.38 mmol). The resulting solution was allowed to stir at ambient temperature for 3 h. The reaction flask was placed in a bath of cold water, then there was added 2N HCl in ether slowly and directly to the reaction mixture. Stirred 5 minutes and then diluted with EtOAc and washed with 1N HCl, sat'd aq sodium bicarbonate and brine, dried (MgSO₄), filtered through a pad of silica gel and concentrated in vacuo to afford Example 12B, benzyl 4-(4-chloro-1H-pyrazolo[3,4-d]pyrimidin-1-yl)piperidine-1-carboxylate, as an oil (2.26 g) which was pure enough to be used without purification. LRMS (ESI): 372.2 (M+H)+.

Example 12

Benzyl 4-(4-(2-fluoro-4-(methylsulfonyl)phenylamino)-1H-pyrazolo[3,4-d]pyrimidin-1-yl)piperidine-1-carboxylate

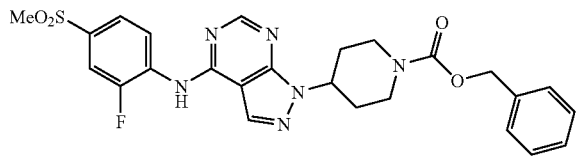

To a solution of benzyl 4-(4-chloro-1H-pyrazolo[3,4-d]pyrimidin-1-yl)piperidine-1-carboxylate from Example 12B (208 mg, 0.56 mmol) in 6 mL of degassed toluene was added 2-fluoro-4-(methylsulfonyl)aniline (106 mg, 0.56 mmol), (±)-BINAP (17 mg, 0.03 mmol), sodium tert-butoxide (54 mg, 0.56 mmol) and Pd(dppf)Cl₂ (complex with CH₂Cl₂, 12 mg, 0.017 mmol). Upon completion of addition, the reaction mixture was heated under microwave irradiation at 110° C. for 1 h. After this time, the reaction mixture was cooled, diluted with ethyl acetate, washed with brine, dried over MgSO₄, and concentrated to yield a residue. The residue was purified by flash chromatography on silica gel (elution with 1:1 hexane/ethyl acetate) to afford 75 mg (26%) of Example 12 as an off-white solid. ¹H NMR (CDCl₃); δ 9.0 (t, 1H, J=8.3 Hz), 8.61 (s, 1H), 8.05 (s, 1H), 7.79 (d, 1H, J=8.8 Hz), 7.74 (dd, 1H, J=10.3, 2.2 Hz), 7.46 (broad s, 1H), 7.37-7.30 (m, 5H), 5.15 (broad s, 2H), 5.00-4.92 (m, 1H), 4.42-4.30 (m, 2H), 3.07 (3, 3H), 3.05-2.95 (m, 2H), 2.30-2.20 (m, 2H), 2.05-1.95 (m, 2H). LRMS (ESI): 525.1 (M+H)+.

Example 13

Isopropyl 4-(4-(2-fluoro-4-(methylsulfonyl)phenylamino)-1H-pyrazolo[3,4-d]pyrimidin-1-yl)piperidine-1-carboxylate

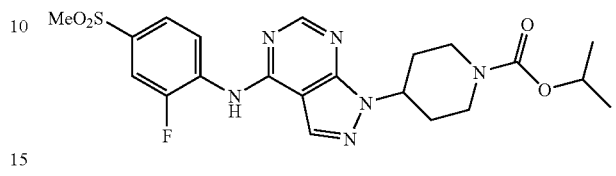

Example 13A

N-(2-Fluoro-4-(methylsulfonyl)phenyl)-1-(piperidin-4-yl)-1H-pyrazolo[3,4-d]pyrimidin-4-amine

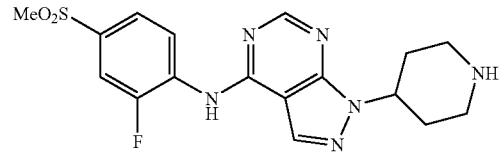

To a solution of benzyl 4-(4-(2-fluoro-4-(methylsulfonyl)phenylamino)-1H-pyrazolo[3,4-d]pyrimidin-1-yl)piperidine-1-carboxylate from Example 12 (250 mg, 4.8 mmol) in 20 mL of absolute ethanol was added 5% Pd/C catalyst (60 mg). The resulting suspension was evacuated and flushed with hydrogen several times, and then was stirred under 1 atm of hydrogen, maintained by a balloon, for 18 h. The mixture was filtered through a pad of CELITE® 545 filter aid and concentrated in vacuo to afford Example 13A (160 mg, 85%) as a yellow oil, which was sufficiently pure to be used without purification. LRMS (EST): 391.2 (M+H)+.

Example 13

Isopropyl 4-(4-(2-fluoro-4-(methylsulfonyl)phenylamino)-1H-pyrazolo[3,4-d]pyrimidin-1-yl)piperidine-1-carboxylate

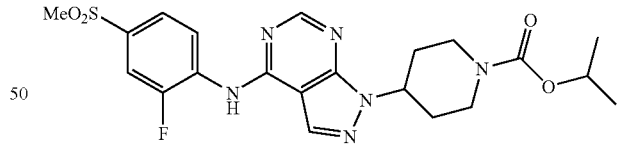

To a solution of N-(2-fluoro-4-(methylsulfonylphenyl)-1-(piperidin-4-yl)-1H-pyrazolo[3,4-d]pyrimidin-4-amine from Example 13A (54 mg, 0.14 mmol) in 4 mL methylene chloride was added triethylamine (0.038 mL, 0.28 mmol) and isopropylchloroformate (0.14 mL of a 1.0 M solution in toluene, 0.14 mmol). The mixture was allowed to stir at room temperature for 1 h. The reaction was diluted with EtOAc and washed with 1N HCl, sat'd aq sodium bicarbonate and brine, dried (MgSO₄), filtered through a pad of silica gel and concentrated in vacuo. The residue was purified by flash chromatography on silica gel (elution with 1:1 hexane/ethyl acetate) to afford 30 mg (45%) of Example 13 as an off-white solid. ¹H NMR (CDCl₃): δ 9.0 (t, 1H, J=8.3 Hz), 8.61 (s, 1H), 8.05 (s, 1H), 7.79 (dd, 1H, J=8.8, 1.7 Hz), 7.75 (dd, 1H, J=10.2, 2.0

Hz), 7.42 (broad s, 1H), 4.98-4.88 (m, 2H), 4.42-4.30 (m, 2H), 3.07 (s, 3H), 3.02-2.92 (m, 2H), 2.28-2.18 (m, 2H), 2.05-1.95 (m, 2N), 1.25 (d, 6H, J=6.1 Hz). LRMS (ESI): 477.2 (M+H)+.

Example 14

N-(2-Fluoro-4-(methylsulfonyl)phenyl)-1-(1-(pyrimidin-2-yl)piperidin-4-yl)-1H-pyrazolo[3,4-d]pyrimidin-4-amine

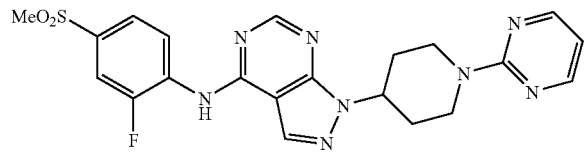

To a solution of N-(2-fluoro-4-(methylsulfonylphenyl)-1-(piperidin-4-yl)-1H-pyrazolo[3,4-d]pyrimidin-4-amine from Example 13A (52 mg, 0.13 mmol) in 2 mL of DMF was added 2-bromopyrimidine (21 mg, 0.13 mmol) and sodium tert-butoxide (12.8 mg, 0.13 mmol). The resulting solution was stirred in a sealed vial at 100° C. for 2 h. The mixture was allowed to cool and was diluted with ethyl acetate, washed with sat'd aq sodium bicarbonate and brine, dried (MgSO$_4$), filtered through a pad of silica gel and concentrated in vacuo to afford a foam. The residue was triturated with ether, and dried in vacuo to afford 30 mg (48%) of Example 14 as a pale yellow powder. $^1$H NMR (CDCl$_3$) δ ppm 2.09 (dd, J=12.37, 2.47 Hz, 2H) 2.29 (ddd, J=24.61, 12.51, 4.12 Hz, 2H) 3.07 (s, 3H) 3.10-3.18 (m, 2H) 4.97 (d, J=13.75 Hz, 2H) 5.04-5.15 (m, 1H) 6.49 (t, J=4.95 Hz, 1H) 7.38 (s, 1H) 7.74 (dd, 1H) 7.80 (d, J=8.80 Hz, 1H) 8.03 (s, 1H) 8.32 (d, J=4.95 Hz, 2H) 8.63 (s, 1H) 9.02 (t, 1H). LRMS (ESI): 469.1 (M+H)+.

Example 15

1-(1-(5-Ethylpyrimidin-2-yl)piperidin-4-yl)-N-(2-fluoro-4-(methylsulfonyl)phenyl)-1H-pyrazolo[3,4-d]pyrimidin-4-amine

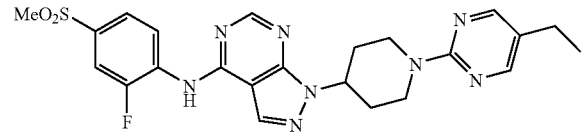

To a solution of N-(2-fluoro-4-(methylsulfonyl)phenyl)-1-(piperidin-4-yl)-1H-pyrazolo[3,4-d]pyrimidin-4-amine from Example 13A (57 mg, 0.15 mmol) in 2 mL of DMF was added 2-chloro-5-ethylpyrimidine (0.18 mL, 0.15 mmol) and sodium tert-butoxide (14 mg, 0.15 mmol). The resulting solution was stirred in a sealed vial at 110° C. for 6 h. The mixture was allowed to cool and was diluted with ethyl acetate, washed with sat'd aq sodium bicarbonate and brine, dried (MgSO$_4$), filtered through a pad of silica gel and concentrated in vacuo to afford a foam. The residue was triturated with warm 2:1 hexane/ethyl acetate, and dried in vacuo to afford 13 mg (18%) of Example 15 as an off-white solid. $^1$H NMR (500 MHz, DMSO) δ ppm 1.14 (t, J=7.56 Hz, 3H) 1.93-2.00 (m, 2H) 2.00-2.07 (m, J=11.91, 3.21 Hz, 2H) 2.44 (q, J=7.79 Hz, 2H) 3.09-3.17 (m, 2H) 3.28 (s, 3H) 4.75 (d, J=12.83 Hz, 2H) 5.00-5.07 (m, 1H) 7.79 (d, J=8.25 Hz, 1H) 7.88 (dd, J=10.08, 1.83 Hz, 1H) 8.22 (t, J=7.79 Hz, 1H) 8.28 (s, 2H) 8.37 (s, 1H) 8.42 (s, 1H). LRMS (ESI): 497.2 (M+H)+.

Example 16

N-(2-Fluoro-4-(methylsulfonyl)phenyl)-1-(1-(5-propylpyrimidin-2-yl)piperidin-4-yl)-1H-pyrazolo[3,4-d]pyrimidin-4-amine

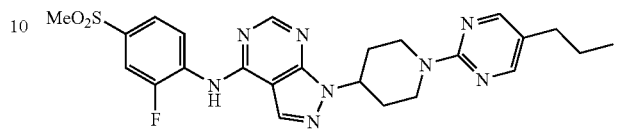

To a solution of N-(2-fluoro-4-(methylsulfonyl)phenyl)-1-(piperidin-4-yl)-1H-pyrazolo[3,4-d]pyrimidin-4-amine from Example 13A (55 mg, 0.14 mmol) in 2 mL of DMF was added 2-chloro-5-propylpyrimidine (0.18 mL, 0.14 mmol) and sodium tert-butoxide (13.5 mg, 0.14 mmol). The resulting solution was stirred in a sealed vial at 100° C. for 18 h. The mixture was allowed to cool and was diluted with ethyl acetate, washed with sat'd aq sodium bicarbonate and brine, dried (MgSO$_4$), filtered through a pad of silica gel and concentrated in vacuo to afford a foam. The residue was triturated with warm ether, and dried in vacuo to afford 15 mg (21%) of Example 16 as an off-white solid. $^1$H NMR (500 MHz, CDCl$_3$) δ ppm 0.93 (t, J=7.42 Hz, 3H) 1.53-1.61 (m, 2H) 2.05-2.11 (m, 2H) 2.24-2.33 (m, 2H) 2.40 (s, 2H) 3.07 (s, 3H) 3.09-3.16 (m, 2H) 3.47 (s, 1H) 4.93 (d, J=13.75 Hz, 2H) 5.04-5.12 (m, 1H) 7.73-7.77 (m, 1H) 7.80 (d, J=8.80 Hz, 1H) 8.03 (s, 1H) 8.17 (s, 2H) 8.62 (s, 1H) 8.98-9.03 (m, 1H). LRMS (ESI): 511.2 (M+H)+.

Example 17

Benzyl 4-(4-(2-methylpyridin-3-yloxy)-1H-pyrazolo[3,4-d]pyrimidin-1-yl)piperidine-1-carboxylate, hydrochloride salt

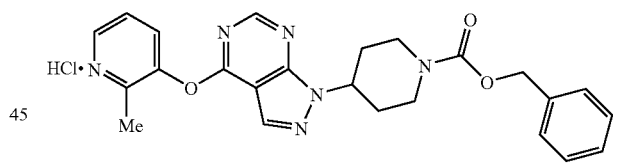

To a solution of benzyl 4-(4-chloro-1H-pyrazolo[3,4-d]pyrimidin-1-yl)piperidine-1-carboxylate from Example 12B (288 mg, 0.78 mmol) in 5 mL of DMF was added 2-methylpyridin-3-ol (85 mg, 0.78 mmol) and potassium carbonate (214 mg, 1.55 mol). The resulting mixture was stirred in a sealed vial at 110° C. for 3 h. The reaction mixture was allowed to cool and was diluted with ethyl acetate, washed with water and brine, dried (MgSO$_4$), and concentrated in vacuo to afford an oil (285 mg). A portion of this residue (18 mg, 0.04 mmol) in 1,4-dioxane (1 mL) and ether (3 mL) was added hydrochloric acid (2N solution in ether, 0.024 mL, 0.048 mmol). The reaction was allowed to stir at room temperature for 10 minutes, at which time a solid had settled out of solution. The solvents were decanted and the solid was triturated with ether and dried in vacuo to afford Example 17 as a pale yellow solid (10 mg, 51%). $^1$H NMR (500 MHz, DMSO) δ ppm 1.96-2.01 (m, 2H) 2.06 (ddd, J=24.06, 12.23, 4.40 Hz, 2H) 2.42 (s, 3H) 3.06-3.18 (m, 2H) 4.16 (d, J=13.20 Hz, 2H) 5.01-5.08 (m, 1H) 5.11 (s, 2H) 7.30-7.39 (m, 5H)

7.58-7.63 (m, 1H) 8.03 (d, J=8.25 Hz, 1H) 8.43 (s, 1H) 8.54 (s, 1H) 8.56 (d, J=5.50 Hz, 1H). LRMS (ESI): 445.2 (M+H)+.

Example 18

Isopropyl 4-(4-(2-methylpyridin-3-yloxy)-1H-pyrazolo[3,4-d]pyrimidin-1-yl)piperidine-1-carboxylate, hydrochloride salt

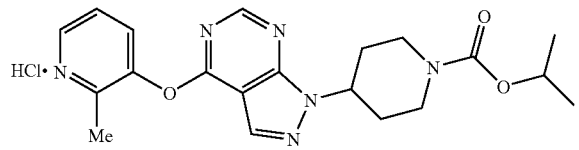

Example 18A 4-(2-Methylpyridin-3-yloxy)-1-(piperidin-4-yl)-1H-pyrazolo[3,4-d]pyrimidine

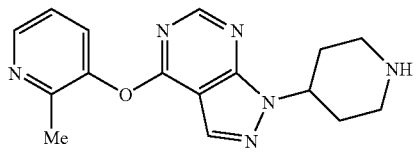

To a solution of benzyl 4-(4-(2-methylpyridin-3-yloxy)-1H-pyrazolo[3,4-d]pyrimidin-1-yl)piperidine-1-carboxylate from Example 18 (210 mg, 0.47 mmol) in 20 mL of absolute ethanol was added 5% Pd/C catalyst (50 mg). The resulting suspension was evacuated and flushed with hydrogen several times, and then was stirred under 1 atm of hydrogen, maintained by a balloon, for 4 h. The mixture was filtered through a pad of CELITE® 545 filter aid and concentrated in vacuo to afford Example 18A (130 mg, 89%) as an oil, which was sufficiently pure to be used without purification. LRMS (ESI): 311.2 (M+H)+.

Example 18

Isopropyl 4-(4-(2-methylpyridin-3-yloxy)-1H-pyrazolo[3,4-d]pyrimidin-1-yl)piperidine-1-carboxylate, hydrochloride salt

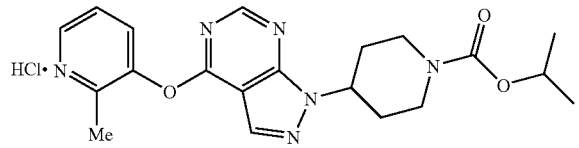

To a solution of 4-(2-methylpyridin-3-yloxy)-1-(piperidin-4-yl)-1H-pyrazolo[3,4-d]pyrimidine from Example 18A (44 mg, 0.14 mmol) in 2 mL of methylene chloride was added triethylamine (0.024 mL, 0.17 mmol) and isopropyl chloroformate (0.14 mL of a 1M solution in toluene, 0.14 mmol). The resulting mixture was allowed to stir at RT overnight. The mixture was diluted with ethyl acetate, washed with sat'd aq sodium bicarbonate and brine, dried (MgSO₄), filtered through a pad of silica gel and concentrated in vacuo to an oil. The residue was purified by silica gel chromatography (12 g ISCO cartridge, 0-100% ethyl acetate/hexane, 15 min gradient) to afford isopropyl 4-(4-(2-methylpyridin-3-yloxy)-1H-pyrazolo[3,4-d]pyrimidin-1-yl)piperidine-1-carboxylate free base (10 mg). Took up in 2 mL ether, added 2N hydrochloric acid (0.07 mL, 0.14 mmol), concentrated to a solid, triturated with hexane and dried in vacuo to afford 8 mg (14%) of Example 18 as an off-white solid. ¹H NMR (500 MHz, CD3OD) δ ppm 1.28 (d, J=6.05 Hz, 6H) 2.00-2.06 (m, 2H) 2.16-2.25 (m, 2H) 2.64 (s, 3H) 3.05-3.16 (m, 2H) 4.26-4.33 (m, 2H) 4.90-4.94 (m, 1H) 5.06-5.13 (m, 1H) 7.94 (dd, J=8.25, 5.50 Hz, 1H) 8.36 (s, 1H) 8.47-8.50 (m, 2H) 8.69 (d, J=4.40 Hz, 1H). LRMS (ESI): 397.2 (M+H)+.

Example 19

Isopropyl 4-(4-(2-cyanopyridin-3-yloxy)-1H-pyrazolo[3,4-d]pyrimidin-1-yl)piperidine-1-carboxylate

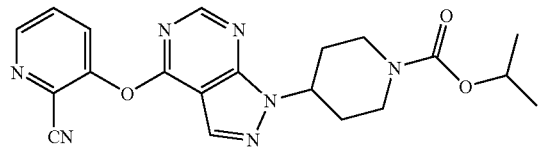

Example 19A

Isopropyl 4-oxopiperidine-1-carboxylate

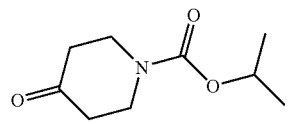

To a solution of tert-butyl 4-oxopiperidine-1-carboxylate (4.0 g, 20.1 mmol) in 30 mL of methylene chloride was added 15 mL of trifluoroacetic acid. The reaction was stirred in a room temperature water bath for 10 min and then the water bath was removed and the reaction was stirred at room temperature for 18 h. The reaction was concentrated in vacuo to afford an oil. This residue was taken up in 60 mL of methylene chloride and then there was added triethylamine (8.39 mL, 60.2 mmol). The reaction flask was placed in a room temperature water bath and then isopropyl chloroformate (20.08 mL of a 1N solution in toluene, 20.08 mmol) was added via addition funnel over about five minutes. The reaction was allowed to stir at room temperature for 2 h. Most of the solvent was removed on a rotary evaporator, and then the reaction was diluted with ethyl acetate, washed with 1N HCl, sat'd aq sodium bicarbonate and brine, dried (MgSO₄), filtered through a pad of silica gel and concentrated in vacuo to afford Example 19A as an oil that was sufficiently pure to be used without purification. ¹H NMR (CDCl₃) δ 4.95 (m, 1H), 3.78-3.70 (m, 4H), 2.48-2.40 (m, 4H), 1.26 (d, 6H, J=6.6 Hz).

Example 19B

Isopropyl 4-(2-(tert-butoxycarbonyl)hydrazinyl)piperidine-1-carboxylate

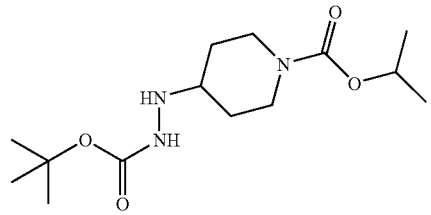

Following the procedure described in Example 12A, isopropyl 4-oxopiperidine-1-carboxylate from Example 19A (1.74 g, 9.39 mmol) was converted into Example 19B (2.48 g, 88%) as a white solid, which was sufficiently pure to be used without purification. LRMS (ESI): 246.3 (M+H)+.

Example 19C

Isopropyl 4-(4-chloro-1H-pyrazolo[3,4-d]pyrimidin-1-yl)piperidine-1-carboxylate

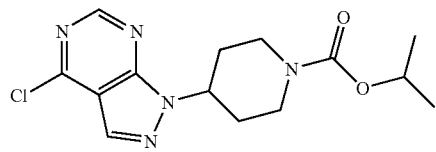

Following the procedure described in Example 12B, isopropyl 4-(2-(tert-butoxycarbonyl)hydrazinyl)piperidine-1-carboxylate from Example 19B (1.74 g, 9.39 mmol) was converted into crude isopropyl 4-(4-chloro-1H-pyrazolo[3,4-d]pyrimidin-1-yl)piperidine-1-carboxylate as an oil. This oil was purified by silica gel chromatography (80 g ISCO cartridge, 0-100% ethyl acetate/hexane) to afford Example 19C (1.58 g, 65%) as a pale yellow oil that solidified on standing. $^1$H NMR (500 MHz, CDCl$_3$) δ ppm 8.72 (s, 1H) 8.12 (s, 1H) 4.98-4.88 (m, 2H) 4.40-4.25 (m, 2H) 3.05-2.92 (m, 2H) 2.28-2.18 (m, 2H) 2.00-1.92 (m, 2H) 1.24 (d, J=6.60 Hz, 6H). LRMS (ESI): 324.2 (M+H)+.

Example 19

Isopropyl 4-(4-(2-cyanopyridin-3-yloxy)-1H-pyrazolo[3,4-d]pyrimidin-1-yl)piperidine-1-carboxylate

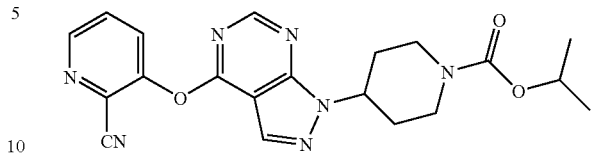

To a solution of isopropyl 4-(4-chloro-1H-pyrazolo[3,4-d]pyrimidin-1-yl)piperidine-1-carboxylate from Example 19C (63 mg, 0.195 mmol) in 2 mL of DMF was added 3-hydroxypicolinonitrile (23.37 mg, 0.195 mmol) and potassium carbonate (53.8 mg, 0.389 mmol). The reaction was allowed to stir at room temperature for 18 h. The reaction was diluted with ethyl acetate, washed with sat'd aq sodium bicarbonate and brine, dried over MgSO$_4$, filtered through a pad of silica gel and concentrated in vacuo to an oil. The residue was purified by silica gel chromatography (12 g ISCO cartridge, 0-90% ethyl acetate/hexane, 15 min gradient) to afford Example 19 (24 mg, 29%) as an off-white solid. $^1$H NMR (500 MHz, CDCl$_3$) δ ppm 1.29 (d, J=6.05 Hz, 6H) 2.02-2.08 (m, 2H) 2.25-2.35 (m, 2H) 2.98-3.08 (m, 2H) 4.38 (s, 2H) 4.94-5.05 (m, 2H) 7.68 (dd, J=8.52, 4.67 Hz, 1H) 7.88 (d, J=8.80 Hz, 1H) 8.27 (s, 1H) 8.49 (s, 1H) 8.69 (d, J=14.40 Hz, 1H). LRMS (ESI): 408.3 (M+H)+.

Examples of Data

Data relevant to the range of activity for compounds of the present invention includes the following data in Table 1.

TABLE 1

| Example No. | Structure | hEC$_{50}$ (nM) | IA |
|---|---|---|---|
| 1 | 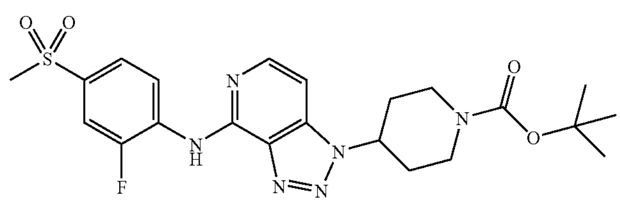 | 1391.00 | 0.55 |
| 2 | 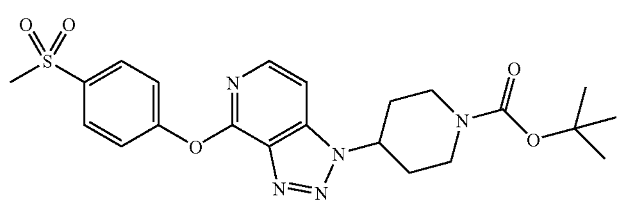 | 3546.00 | 0.29 |
| 3 | 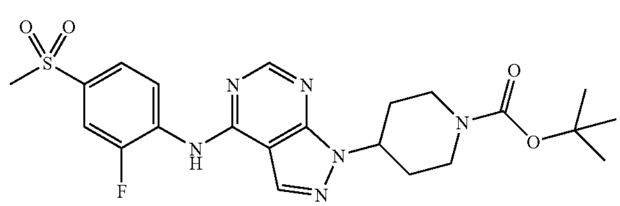 | 19.49 | 0.69 |

TABLE 1-continued

| Example No. | Structure | hEC$_{50}$ (nM) | IA |
|---|---|---|---|
| 4 | 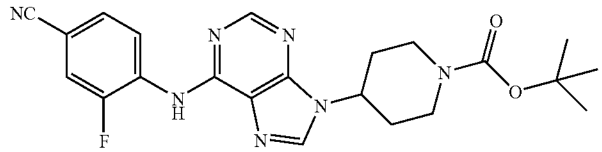 | 287.40 | 0.70 |
| 5 | 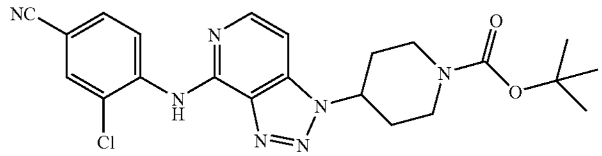 | 411.10 | 0.27 |
| 6 | 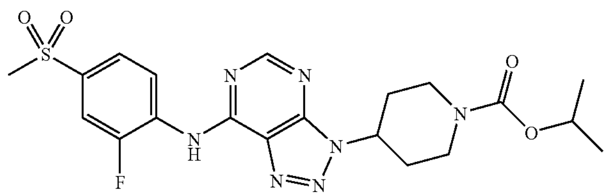 | 139.60 | 0.86 |
| 7 | 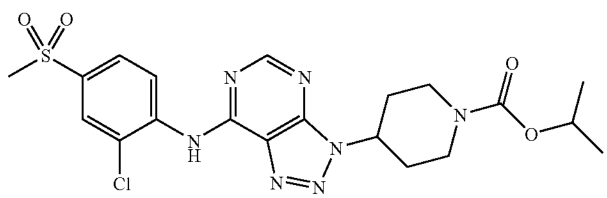 | 74.94 | 0.68 |
| 8 | 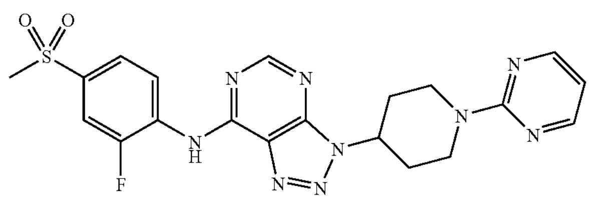 | 217.70 | 0.67 |
| 9 | 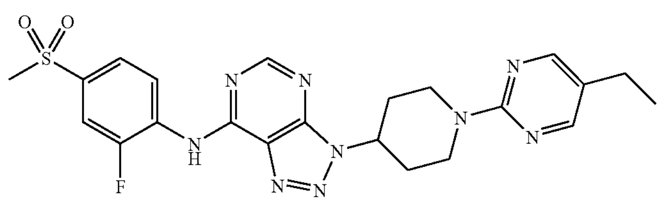 | 263.10 | 0.56 |
| 10 | 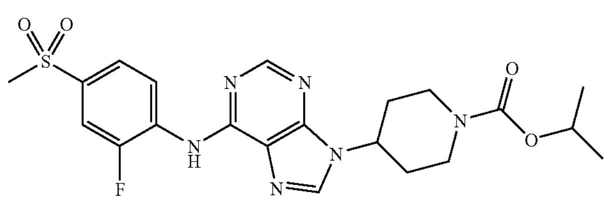 | 407.30 | 0.79 |
| 11 | 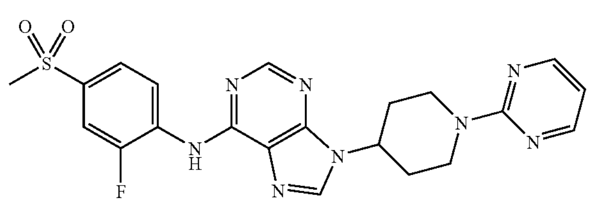 | 366.70 | 0.81 |

TABLE 1-continued

| Example No. | Structure | hEC₅₀ (nM) | IA |
|---|---|---|---|
| 12 | MeO₂S-C₆H₃(F)-NH-[pyrazolopyrimidine]-N-piperidine-N-C(O)O-CH₂-phenyl | 203.20 | 0.47 |
| 13 | MeO₂S-C₆H₃(F)-NH-[pyrazolopyrimidine]-N-piperidine-N-C(O)O-iPr | 308.40 | 0.69 |
| 14 | MeO₂S-C₆H₃(F)-NH-[pyrazolopyrimidine]-N-piperidine-N-pyrimidine | 544.60 | 0.76 |
| 15 | MeO₂S-C₆H₃(F)-NH-[pyrazolopyrimidine]-N-piperidine-N-(5-ethyl-pyrimidine) | 76.16 | 0.94 |
| 16 | MeO₂S-C₆H₃(F)-NH-[pyrazolopyrimidine]-N-piperidine-N-(5-propyl-pyrimidine) | 81.75 | 1.11 |
| 17 | HCl·(2-Me-pyridin-3-yl)-O-[pyrazolopyrimidine]-N-piperidine-N-C(O)O-CH₂-phenyl | 1899.00 | 0.31 |
| 18 | HCl·(2-Me-pyridin-3-yl)-O-[pyrazolopyrimidine]-N-piperidine-N-C(O)O-iPr | 2716.00 | 0.17 |
| 19 | (2-CN-pyridin-3-yl)-O-[pyrazolopyrimidine]-N-piperidine-N-C(O)-CH₂-CH(CH₃)₂ | 505.10 | 0.13 |

What is claimed is:

1. A compound of Formula Ia

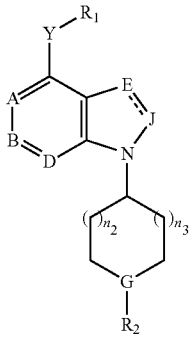

Formula Ia or an enantiomer, diastereomer, or a pharmaceutically acceptable salt thereof wherein:

A and D are each independently selected to be N;
B is selected to be CR$_{4b}$;
E is selected from the group consisting of N and NH;
G is N;
J is N;
the dashed line represents an optional double bond;
Y is —NR$_3$, O or S;
n$_2$ and n$_3$ are each independently 0-2;
R$_1$ is aryl, which may be optionally substituted with one or more substituents selected from R$_4$;
R$_2$ is selected from the group consisting of cycloalkyl, aryl, heteroaryl, heterocyclyl, —C(=O)R$_5$ and —C(=O)OR$_5$, wherein the cycloalkyl, aryl, heteroaryl and heterocyclyl may each be optionally substituted with one or more R$_6$'s;
R$_3$ is selected from the group consisting of hydrogen, alkyl, alkoxy, cycloalkyl, aryl, arylalkyl, heteroaryl, heteroarylalkyl, heterocyclyl and heterocyclylalkyl;
R$_4$, at each occurrence, is independently selected from the group consisting of alkyl, aryl, alkenyl, alkynyl, cycloalkyl, heteroaryl, heterocyclyl, halo, —CN, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, alkenyl, alkynyl, cycloalkyl, heteroaryl and heterocyclyl may each be optionally substituted with one or more R$_6$'s;
R$_{4b}$, at each occurrence, is independently selected from the group consisting of hydrogen, alkyl, haloalkyl, aryl, alkenyl, alkynyl, cycloalkyl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, alkenyl, alkynyl, cycloalkyl, heteroaryl and heterocyclyl may each be optionally substituted with one or more R$_6$'s;
R$_5$ is selected from the group consisting of alkyl, aryl, cycloalkyl, heteroaryl and heterocyclyl, each of which may optionally be substituted with one or more R$_6$'s;
R$_6$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$;
R$_8$, at each occurrence, is independently selected from the group consisting of alkyl, aryl, cycloalkyl, heteroaryl and heterocyclyl;
R$_9$, at each occurrence, is independently selected from the group consisting of hydrogen, alkyl, alkoxy, cycloalkyl, aryl, arylalkyl, heteroaryl, heteroarylalkyl, heterocyclyl and heterocyclylalkyl, wherein the aryl, arylalkyl, heteroaryl, heteroarylalkyl, heterocyclyl and heterocyclylalkyl may each be optionally substituted with 0-5 R$_{9a}$, and the heteroaryl, heteroarylalkyl, heterocyclyl and heterocyclylalkyl each contain 1-4 heteroatoms selected from N, O and S;
R$_{9a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;
R$_{10}$, at each occurrence, is independently selected from the group consisting of alkyl, cycloalkyl, alkenyl, alkynyl, aryl, arylalkyl, heteroaryl, heteroarylalkyl, heterocyclyl and heterocyclylalkyl, wherein the aryl, arylalkyl, heterocyclyl and heterocyclylalkyl may each be optionally substituted with 0-5 R$_{10a}$, and the heterocyclyl and heterocyclylalkyl each contain 1-4 heteroatoms selected from N, O and S;
R$_{10a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)

$NR_{14}R_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl; and R$_{14}$, at each occurrence, is independently selected from the group consisting of hydrogen, alkyl, cycloalkyl and aryl.

2. A compound according to claim 1, wherein:

J is N;

the dashed line represents an optional double bond;

Y is —NR$_3$, O or S;

n$_2$ and n$_3$ are independently 1 or 2;

R$_1$ is aryl, which may be optionally substituted with one or more substituents selected from R$_4$;

R$_2$ is selected from the group consisting of cycloalkyl, aryl, heteroaryl, heterocyclyl, —C(=O)R$_5$ and —C(=O)OR$_5$, wherein the cycloalkyl, aryl, heteroaryl and heterocyclyl may each be optionally substituted with one or more R$_6$'s;

R$_3$ is hydrogen, alkyl or cycloalkyl;

R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may each be optionally substituted with one or more R$_6$'s;

R$_{4b}$, at each occurrence, is independently selected from the group consisting of hydrogen, alkyl, haloalkyl, cycloalkyl, halo, CN, —OH, —OR$_{10}$, —SR$_{10}$, aryl, heteroaryl and heterocyclyl, wherein the alkyl, cycloalkyl, aryl, heteroaryl and heterocyclyl may each be optionally substituted with one or more R$_6$'s;

R$_5$ is alkyl, aryl, cycloalkyl, heteroaryl or heterocyclyl, each of which may be optionally substituted with one or more R$_6$'s;

R$_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$;

R$_8$, at each occurrence, is independently selected from the group consisting of alkyl, aryl, cycloalkyl, heteroaryl and heterocyclyl;

R$_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may each be optionally substituted with 0-5 R$_{9a}$, and the heteroaryl and heterocyclyl each contain 1-4 heteroatoms selected from N, O and S;

R$_{9a}$, at each occurrence, is independently selected from the group consisting of C1-6 alkyl, C1-4 haloalkyl, C6-10 aryl, C3-6 cycloalkyl, heteroaryl, heterocyclyl, halo, —NH$_2$, —CN, —C(=O)OH, —C(=O)OR$_{14}$, —OCF$_3$, —OR$_{14}$ and —OH;

R$_{10}$, at each occurrence, is independently selected from the group consisting of alkyl, cycloalkyl, aryl, heteroaryl and heterocyclyl, wherein the aryl, heteroaryl and heterocyclyl may be each optionally substituted with 0-5 R$_{10a}$, and the heteroaryl and heterocyclyl each contain 1-4 heteroatoms selected from N, O and S;

R$_{10a}$, at each occurrence, is independently selected from the group consisting of C1-6 alkyl, C1-4 haloalkyl, C6-10 aryl, C3-6 cycloalkyl, heteroaryl, heterocyclyl, halo, —NH$_2$, —CN, —C(=O)OH, —C(=O)OR$_{14}$, —OCF$_3$, —OR$_{14}$ and —OH; and R$_{14}$, at each occurrence, is independently selected from the group consisting of hydrogen, C1-6 alkyl, C3-6 cycloalkyl and C6-10 aryl.

3. A compound according to claim 1, wherein:

J is N;

the dashed line represents an optional double bond;

Y is —NR$_3$, O or S;

n$_2$ and n$_3$ are independently 1 or 2;

R$_1$ is aryl, which may be optionally substituted with one or more substituents selected from R$_4$;

R$_2$ is aryl, heteroaryl, heterocyclyl, —C(=O)R$_5$ or —C(=O)OR$_5$, wherein the aryl, heteroaryl and heterocyclyl may each be optionally substituted with one or more R$_6$'s;

R$_3$ is hydrogen or alkyl;

R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may each be optionally substituted with one or more R$_6$'s;

R$_{4b}$, at each occurrence, is independently selected from the group consisting of hydrogen, C1-6 alkyl, C1-4 haloalkyl, C6-10 aryl, C3-6 cycloalkyl, halo, CN, —OH, —OR$_{10}$ and —SR$_{10}$, wherein the alkyl, cycloalkyl and aryl may each be optionally substituted with one or more R$_6$'s;

R$_5$ is selected from the group consisting of C1-6 alkyl, C6-10 aryl, C3-6 cycloalkyl, heteroaryl and heterocyclyl, each of which may be optionally substituted with one or more R$_6$'s;

R$_6$, at each occurrence, is independently selected from the group consisting of C1-6 alkyl, C1-4 haloalkyl, C6-10 aryl, C3-6 cycloalkyl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently selected from the group consisting of C1-6 alkyl, C6-10 aryl, C3-6 cycloalkyl, heteroaryl and heterocyclyl;

$R_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may each be optionally substituted with 0-5 $R_{9a}$, and the heteroaryl and heterocyclyl each contain 1-4 heteroatoms selected from N, O and S;

$R_{9a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH;

$R_{10}$, at each occurrence, is independently selected from the group consisting of C1-6 alkyl, C3-6 cycloalkyl, C6-10 aryl, heteroaryl and heterocyclyl, wherein the aryl, heteroaryl and heterocyclyl may each be optionally substituted with 0-5 $R_{10a}$, and the heteroaryl and heterocyclyl each contains 1-4 heteroatoms selected from N, O and S;

$R_{10a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH; and $R_{14}$, at each occurrence, is independently selected from the group consisting of hydrogen, C1-6 alkyl and C6-10 aryl.

4. The compound of claim 1, including an enantiomer, diastereomer, or salt thereof, wherein:

J is N;

the dashed line represents an optional double bond;

Y is —$NR_3$, O or S;

$n_2$ and $n_3$ are independently 1 or 2;

$R_1$ is C6-10 aryl, which may be optionally substituted with one or more substituents selected from $R_4$;

$R_2$ is C6-10 aryl, heteroaryl, —C(=O)$R_5$ or —C(=O)$OR_5$, wherein the aryl and heteroaryl may each be optionally substituted with one or more $R_6$'s;

$R_3$ is hydrogen or C1-4 alkyl;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —$SR_{10}$, —S(O)$_3$H, —P(O)$_3H_2$, —C(=O)$NR_9R_9$, —$NR_9R_9$, —S(O)$_2NR_9R_9$, —$NR_9S$(O)$_2CF_3$, —C(=O)$NR_9S(O)_2R_9$, —S(O)$_2NR_9C$(=O)$OR_9$, —S(O)$_2NR_9C$(=O)$NR_9R_9$, —C(=O)$NR_9S(O)_2$$CF_3$, —C(=O)$R_{10}$, —$NR_9C$(=O)H, —$NR_9C$(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —S(O)$_2R_{10}$, —$NR_9C$(=O)$OR_8$ and —$NR_9S(O_2)R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl, C1-4 haloalkyl, C6-10 aryl, C3-6 cycloalkyl, halo, CN, —OH, —$OR_{10}$ and —$SR_{10}$, wherein the alkyl, cycloalkyl and aryl may each be optionally substituted with one or more $R_6$'s;

$R_5$ is C1-6 alkyl, C6-10 aryl, C3-6 cycloalkyl or heteroaryl each of which may be optionally substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —$SR_{10}$, —S(O)$_3$H, —P(O)$_3H_2$, —C(=O)$NR_9R_9$, —$NR_9R_9$, —S(O)$_2NR_9R_9$, —$NR_9S$(O)$_2CF_3$, —C(=O)$NR_9S(O)_2R_9$, —S(O)$_2NR_9C$(=O)$OR_9$, —S(O)$_2NR_9C$(=O)$NR_9R_9$, —C(=O)$NR_9S(O)_2$$CF_3$, —C(=O)$R_{10}$, —$NR_9C$(=O)H, —$NR_9C$(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, —$NR_9C$(=O)$OR_8$ and —$NR_9S(O_2)R_8$;

$R_8$, at each occurrence, is independently selected from the group consisting of C1-6 alkyl, C6-10 aryl, C3-6 cycloalkyl and heteroaryl;

$R_9$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 $R_{9a}$, and the heteroaryl contains 1-4 heteroatoms selected from N, O and S;

$R_{9a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH;

$R_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 $R_{10a}$, and the heteroaryl contains 1-4 heteroatoms selected from N, O and S;

$R_{10a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH; and $R_{14}$, at each occurrence, is independently selected from the group consisting of hydrogen, C1-6 alkyl and C6-10 aryl.

5. A compound according to claim 1, wherein:

J is N;

the dashed line represents a double bond;

Y is —$NR_3$, O or S;

$n_2$ and $n_3$ are each independently 1 or 2;

$R_1$ is C6-10 aryl, which may be optionally substituted with one or more substituents selected from $R_4$;

$R_2$ is heteroaryl, —C(=O)$R_5$ or —C(=O)$OR_5$, wherein the heteroaryl may be optionally substituted with one or more $R_6$'s;

$R_3$ is hydrogen;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —$SR_{10}$, —S(O)$_3$H, —P(O)$_3H_2$, —C(=O)$NR_9R_9$, —$NR_9R_9$, —S(O)$_2NR_9R_9$, —$NR_9S$(O)$_2CF_3$, —C(=O)$NR_9S(O)_2R_9$, —S(O)$_2NR_9C$(=O)$OR_9$, —S(O)$_2NR_9C$(=O)$NR_9R_9$, —C(=O)$NR_9S(O)_2$$CF_3$, —C(=O)$R_{10}$, —$NR_9C$(=O)H, —$NR_9C$(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —S(O)$_2R_{10}$, —$NR_9C$(=O)$OR_8$ and —$NR_9S(O_2)R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl, C6-10 aryl and C3-6 cycloalkyl, wherein the alkyl, cycloalkyl, and aryl may each be optionally substituted with one or more $R_6$'s;

$R_5$ is C1-6 alkyl, C6-10 aryl or C3-6 cycloalkyl, each of which may be optionally substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently C1-6 alkyl or C6-10 aryl;

$R_9$, at each occurrence, is independently hydrogen, C1-6 alkyl, C3-6 cycloalkyl, C6-10 aryl or heteroaryl, wherein the aryl and heteroaryl may each be optionally substituted with 0-5 $R_{9a}$, and the heteroaryl contains 1-4 heteroatoms selected from N, O and S;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

$R_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 $R_{10a}$, and the heteroaryl contains 1-4 heteroatoms selected from N, O and S;

$R_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and $R_{14}$, at each occurrence, is independently selected from the group consisting of hydrogen, C1-6 alkyl and C6-10 aryl.

6. A compound according to claim 1, wherein:

J is N;

the dashed line represents a double bond;

Y is —NR$_3$, O or S;

$n_2$ and $n_3$ are independently 1 or 2;

$R_1$ is C6-10 aryl, which may be optionally substituted with one or more substituents selected from $R_4$;

$R_2$ is heteroaryl, —C(=O)R$_5$ or —C(=O)OR$_5$, wherein the heteroaryl may be optionally substituted with one or more $R_6$'s;

$R_3$ is hydrogen;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl and C3-6 cycloalkyl, wherein the alkyl and cycloalkyl may each be optionally substituted with one or more $R_6$'s;

$R_5$ is C1-6 alkyl, C6-10 aryl or C3-6 cycloalkyl, each of which may be optionally substituted with one or more $R_6$'s;

$R_6$, at each occurrence, is independently selected from the group consisting of C1-6 alkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently C1-6 alkyl or C6-10 aryl;

$R_9$, at each occurrence, is independently hydrogen, C1-6 alkyl, C3-6 cycloalkyl or C6-10 aryl, wherein the aryl may be optionally substituted with 0-5 $R_{9a}$;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

$R_{10}$, at each occurrence, is independently hydrogen, C1-6 alkyl, C3-6 cycloalkyl or C6-10 aryl, wherein the aryl may be optionally substituted with 0-5 $R_{10a}$;

$R_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and $R_{14}$, at each occurrence, is independently selected from the group consisting of hydrogen, C1-6 alkyl and C6-10 aryl.

7. The compound of claim 1, including an enantiomer, diastereomer, or salt thereof, wherein:

A and D are each independently N;

B is CH;

E is N;

G is N;

J is N;

the dashed line is a double bond;

Y is —NR$_3$ or O;

$n_2$ and $n_3$ are 1;

$R_1$ is phenyl, which may be optionally substituted with 1-5 of $R_4$;

$R_2$ is heteroaryl, —C(=O)R$_5$ or —C(=O)OR$_5$, wherein the heteroaryl may be optionally substituted with 1-5 of $R_6$'S;

$R_3$ is hydrogen;

$R_4$, at each occurrence, is independently selected from the group consisting of C1-6 alkyl, C1-4 haloalkyl, C3-6 cycloalkyl, phenyl, heteroaryl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, phenyl and heteroaryl may each be optionally substituted with 1-5 of $R_6$'s;

$R_5$ is C1-6 alkyl, C3-6 cycloalkyl or phenyl, each of which may be optionally substituted with 1-5 of $R_6$'s;

$R_6$, at each occurrence, is independently selected from the group consisting of C1-6 alkyl, C1-4 haloalkyl, C3-6 cycloalkyl, phenyl, heteroaryl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR₉R₉, —S(=O)R₁₀, —S(O)₂R₁₀, —NR₉C(=O)OR₈ and —NR₉S(O₂)R₈;

R₈, at each occurrence, is independently C1-6 alkyl or phenyl;

R₉, at each occurrence, is independently hydrogen, C1-6 alkyl, C3-6 cycloalkyl or phenyl, wherein the phenyl may be optionally substituted with 0-5 R₉ₐ;

R₉ₐ, at each occurrence, is independently selected from the group consisting of C1-6 alkyl, halo, —NH₂, —CN, —C(=O)OH, —C(=O)OR₁₄, —OCF₃, —OR₁₄ and —OH;

R₁₀, at each occurrence, is independently hydrogen, C1-6 alkyl, C3-6 cycloalkyl or phenyl, wherein the phenyl may be optionally substituted with 0-5 R₁₀ₐ;

R₁₀ₐ, at each occurrence, is independently selected from the group consisting of C1-6 alkyl, halo, —NH₂, —CN, —C(=O)OH, —C(=O)OR₁₄, —OCF₃, —OR₁₄ and —OH; and R₁₄, at each occurrence, is independently selected from the group consisting of hydrogen, C1-6 alkyl and phenyl.

8. The compound of claim 1, including an enantiomer, diastereomer, or salt thereof, wherein:

A and D are independently N;
B is CH;
E is N;
G is N;
J is N;
the dashed line is a double bond;
Y is —NR₃ or O;
n₂ and n₃ are 1;
R₁ is phenyl, which may be optionally substituted with 1-5 of R₄;
R₂ is —C(=O)OR₅ or a heteroaryl selected from the group consisting of pyrimidinyl, pyridyl, oxadiazolyl and benzoxazole, wherein the heteroaryl may be optionally substituted with 1-5 of R₆'s;
R₃ is hydrogen;
R₄, at each occurrence, is independently selected from the group consisting of C1-6 alkyl, C1-4 haloalkyl, C3-6 cycloalkyl, phenyl, heteroaryl which has a single ring with 6 atoms of which 1-3 are selected from O, S and N, halo, —CN, —C(=O)OH, —C(=O)OR₁₀, —OCF₃, —OR₁₀, —OH, —SR₁₀, —C(=O)NR₉R₉, —NR₉R₉, —S(O)₂NR₉R₉, —C(=O)NR₉S(O)₂R₉, —S(O)₂NR₉C(=O)OR₉, —C(=O)R₁₀, —NR₉C(=O)H, —NR₉C(=O)R₁₀, —OC(=O)NR₉R₉, —S(=O)R₁₀, —S(O)₂R₁₀, —NR₉C(=O)OR₈ and —NR₉S(O₂)R₈, wherein the alkyl, phenyl and heteroaryl may each be optionally substituted with 1-5 of R₆'s;
R₅ is C1-6 alkyl, C3-6 cycloalkyl or phenyl, each of which may be optionally substituted with 1-5 of R₆'s;
R₆, at each occurrence, is independently selected from the group consisting of C1-6 alkyl, C1-4 haloalkyl, C3-6 cycloalkyl, phenyl, heteroaryl, halo, —CN, —C(=O)OH, —C(=O)OR₁₀, —OCF₃, —OR₁₀, —OH, —SR₁₀, —C(=O)NR₉R₉, —NR₉R₉, —S(O)₂NR₉R₉, —C(=O)NR₉S(O)₂R₉, —S(O)₂NR₉C(=O)OR₉, —C(=O)R₁₀, —NR₉C(=O)H, —NR₉C(=O)R₁₀, —OC(=O)NR₉R₉, —S(=O)R₁₀, —S(O)₂R₁₀, —NR₉C(=O)OR₈ and —NR₉S(O₂)R₈;

R₈, at each occurrence, is independently C1-6 alkyl or phenyl;

R₉, at each occurrence, is independently hydrogen, C1-6 alkyl, C3-6 cycloalkyl or phenyl, wherein the phenyl may be optionally substituted with 0-5 R₉ₐ;

R₉ₐ, at each occurrence, is independently selected from the group consisting of C1-6 alkyl, halo, —NH₂, —CN, —C(=O)OH, —C(=O)OR₁₄, —OCF₃, —OR₁₄ and —OH;

R₁₀, at each occurrence, is independently selected from the group consisting of C1-6 alkyl, C3-6 cycloalkyl and phenyl, wherein the phenyl may be optionally substituted with 0-5 R₁₀ₐ;

R₁₀ₐ, at each occurrence, is independently selected from the group consisting of C1-6 alkyl, halo, —NH₂, —CN, —C(=O)OH, —C(=O)OR₁₄, —OCF₃, —OR₁₄ and —OH; and R₁₄, at each occurrence, is independently selected from the group consisting of hydrogen and C1-6 alkyl.

9. A compound according to claim 1 selected from the group consisting of:

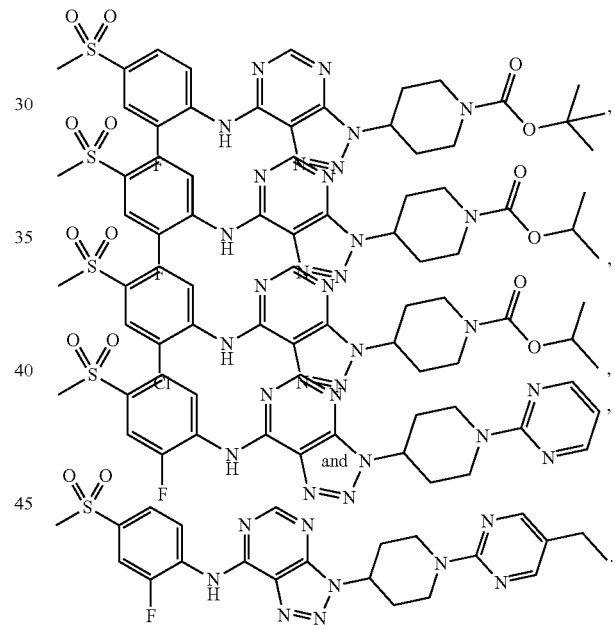

10. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 8,093,257 B2  
APPLICATION NO. : 12/112053  
DATED : January 10, 2012  
INVENTOR(S) : John Fevig et al.

Page 1 of 3

It is certified that error appears in the above-identified patent and that said Letters Patent is hereby corrected as shown below:

On the Title Page, Col. 2, Item [56] Other Publications, line 16-18, After "1-24 (2001)." delete "Boger, D.L. et al., "Total Syntheses of Azafluoranthene Alkaloids: Rufescine and Imeluteine", J. Org. Chem., vol. 49, No. 21, pp. 4050-4055 (1984)." and insert the same on First Page, Col. 2, Line 17, as a new entry.

In the Claims

Claim 1, col. 74, line 59, after "heterocyclyl" insert -- , --;

Claim 9, col. 82, Line 26-50, structure, delete

Signed and Sealed this  
Thirtieth Day of April, 2013

Teresa Stanek Rea  
*Acting Director of the United States Patent and Trademark Office*

CERTIFICATE OF CORRECTION (continued)
U.S. Pat. No. 8,093,257 B2

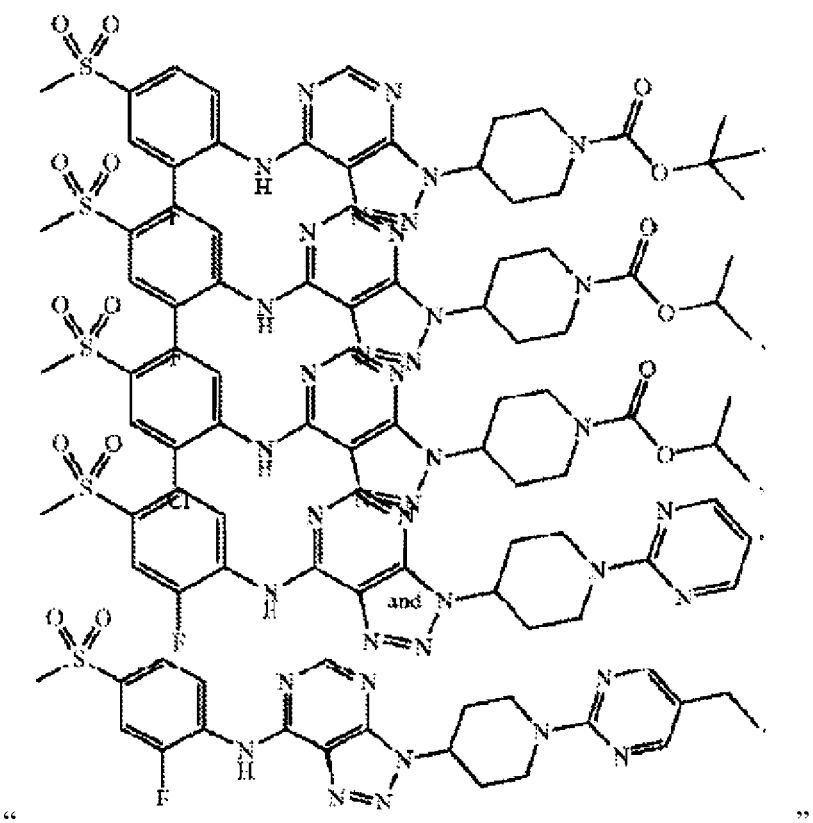

"                                                                    "

Claim 9, col. 82, Line 26-50, structure, insert

CERTIFICATE OF CORRECTION (continued)
U.S. Pat. No. 8,093,257 B2

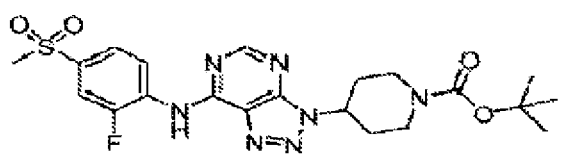

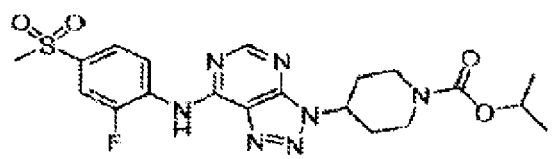

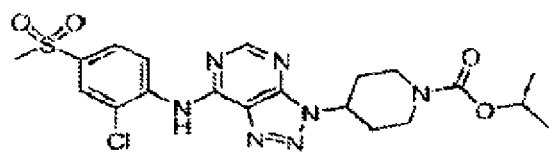

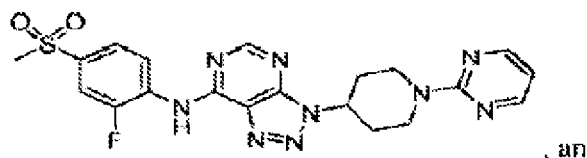, and

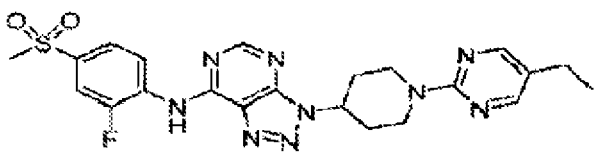

-- --, therefor.